US008829051B2

(12) United States Patent
Gurtner et al.

(10) Patent No.: US 8,829,051 B2
(45) Date of Patent: Sep. 9, 2014

(54) METHOD OF TREATING OR PREVENTING PATHOLOGIC EFFECTS OF ACUTE INCREASES IN HYPERGLYCEMIA AND/OR ACUTE INCREASES OF FREE FATTY ACID FLUX

(75) Inventors: Geoffrey C. Gurtner, New York, NY (US); Michael A. Brownlee, New York, NY (US)

(73) Assignee: Geoffrey C. Gurtner, Stanford, CA (US)

( * ) Notice: Subject to any disclaimer, the term of this patent is extended or adjusted under 35 U.S.C. 154(b) by 0 days.

(21) Appl. No.: 11/136,254

(22) Filed: May 24, 2005

(65) Prior Publication Data
US 2006/0100189 A1     May 11, 2006

Related U.S. Application Data

(60) Provisional application No. 60/573,947, filed on May 24, 2004.

(51) Int. Cl.
| | | |
|---|---|---|
| A61K 31/13 | (2006.01) | |
| A61K 31/19 | (2006.01) | |
| A61K 31/385 | (2006.01) | |
| A61K 31/555 | (2006.01) | |
| A61K 31/198 | (2006.01) | |

(52) U.S. Cl.
CPC ............. *A61K 31/385* (2013.01); *A61K 31/555* (2013.01); *A61K 31/198* (2013.01)
USPC .......................................... 514/575; 514/645

(58) Field of Classification Search
USPC ................... 514/5.4, 440, 836, 886, 575, 645
See application file for complete search history.

(56) References Cited

U.S. PATENT DOCUMENTS

| | | | |
|---|---|---|---|
| 5,047,427 A | | 9/1991 | Williamson |
| 5,382,574 A * | | 1/1995 | Jorgensen ........................ 514/3 |
| 5,677,330 A | | 10/1997 | Abraham et al. |
| 6,337,350 B1 | | 1/2002 | Rahbar et al. |
| 6,348,465 B1 * | | 2/2002 | Baker ........................... 514/248 |
| 6,576,653 B2 | | 6/2003 | Du Bois |
| 6,579,544 B1 | | 6/2003 | Rosenberg et al. |
| 6,737,421 B1 * | | 5/2004 | Lubish et al. .................. 514/218 |
| 2003/0060408 A1 * | | 3/2003 | Bar-Or et al. ..................... 514/12 |
| 2003/0069273 A1 | | 4/2003 | Lattmann et al. |
| 2004/0029851 A1 * | | 2/2004 | Murphy et al. ................ 514/184 |
| 2005/0215468 A1 | | 9/2005 | Bar-Or et al. |
| 2006/0281748 A1 | | 12/2006 | Gurtner et al. |

FOREIGN PATENT DOCUMENTS

| | | | |
|---|---|---|---|
| EP | 1374868 | * | 1/2004 |
| JP | 05 009114 A | | 1/1993 |
| WO | WO 00/19993 | | 4/2000 |
| WO | WO 00/19993 A | | 4/2000 |
| WO | WO0191774 A2 | * | 12/2001 ............. A61K 35/12 |
| WO | WO 02/098431 A | | 12/2002 |
| WO | WO 2004/039430 A2 | | 5/2004 |
| WO | WO 2005/060986 | | 7/2005 |
| WO | WO 2005/060986 A | | 7/2005 |
| WO | WO 2005/115379 | | 12/2005 |

OTHER PUBLICATIONS

Muha, Local wound care in diabetic foot complications. Postgraduate Medicine vol. 106 No. 1 (1999).*
Kipshidze et al.; "Therapeutic angiogenesis for patients with limb ischemia by utilization of fibrin meshwork: Pilot randomized controlled study"; Dec. 2003; International Angiology; 22(4): 349-55.*
Chekanov et al.; "Deferoxamine Enhances Neovascularization and Recovery of Ischemic Skeletal Muscle in an Experimental Sheep Model"; Jan. 2003; The Annals of Thoracic Surgery; 75(1); 184-9.*
Arana-Conejo, et al.; "Physiopathology of Complications of Diabetic Foot"; May-Jun. 2003; Gac. Med. Mex.; 193(3): 255-64; PubMed abstract; PMID: 12872418.*
Cameron, N.E., et al. Journal of Clinical Investigation vol. 96, pp. 1159-1163. Published 1995.*
Fraga, C.G. et al., Toxicology vol. 180, pp. 23-32. Published 2002.*
Rose, C. et al. Annals of the New York Academy of Sciences. vol. 850, pp. 488-489. Jun. 1998.*
Ress, A.M. et al. Ann. Plast. Surg. vol. 34 pp. 388-395. Published 1995.*
Chatterjee et al., "Inhibitors of Poly (ADP-Ribose) Synthetase Protect Rat Proximal Tubular Cells Against Oxidant Stress," *Kidney International* 56:973-984 (1999).
Thomson PDR, "DESFERAL® (Novartis) (Deferoxamine Mesylate for Injection USP) Vials, Rx only," (copyright 2002-2005) at http://www.thomsonhc.com/pdrel.librarian/ND_PR/Pdr/PFPUI/jT4KPFaZgOiHC/DDAK . . . (visited Oct. 11, 2005).
Meijler, et al. "Synthesis and Evaluation of Iron Chelators with Masked Hydrophilic Moieties." J. Am. Chem. Soc., 2002,124:43, pp. 12666-12667.
The International Search Report for PCT Application No. PCT/US06/46446, dated Oct. 18, 2007.
The Written Opinion of the International Searching Authority for PCT Application No. PCT/US06/46446, dated Oct. 18, 2007.
U.S. Appl. No. 11/297,808, filed Dec. 7, 2005.
USPTO Office Action dated Dec. 17, 2007 in connection with U.S. Appl. No. 11/297,808, filed Dec. 7, 2005.
USPTO Office Action dated Sep. 24, 2008 in connection with U.S. Appl. No. 11/297,808, filed Dec. 7, 2005.
The Partial European Search Report for PCT Application No. PCT/US2005/018069.
Curio et al. "Decreased cultured endothelial cell proliferation in high glucose medium is reversed by antioxidants: new insights on the parthophysiological mechanisms of diabetic vascular complications." In Vitro Celllular & Developmental Biology, vol. 28A, No. 11/12 (1992), pp. 787-790.

(Continued)

*Primary Examiner* — Paul Zarek
*Assistant Examiner* — George W Kosturko
(74) *Attorney, Agent, or Firm* — Medlen & Carroll, LLP

(57) ABSTRACT

One aspect of the present invention relates to a method of treating or preventing pathologic sequelae of acute hyperglycemia and/or increased fatty acid flux in a subject. This method involves administering an ROS inhibitor to the subject. In addition, methods of promoting neovascularization, inhibiting oxidation or excessive release of free fatty acids, and identifying compounds suitable for treatment or prevention of ROS-mediated injury are also disclosed.

10 Claims, 40 Drawing Sheets

(56) References Cited

OTHER PUBLICATIONS

Giardino et al. "BCL-2 expression or antioxidants prevent hyperglycemia-induced formation of intracellular advanced glycation endproducts in bovine endothelial cells." Journal of Clinical Investigation, vol. 97, No. 6 (1996), pp. 1422-1428.

USPTO Office Action dated Jan. 13, 2010 in connection with U.S. Appl. No. 11/297,808, filed Dec. 7, 2005.

USPTO Office Action dated Jun. 3, 2009 in connection with U.S. Appl. No. 11/297,808, fled Dec. 7, 2005.

Hattori N et al., entitled "Deferoxamine improves coronary vascular responses to sympathetic stimulation in patients with type 1 diabetes mellitus," European Journal of Nuclear Medicine, vol. 29, No. 7, Jul. 2002, 891-898.

Grundy S M, entitled "Cadiovascular and Metabolic Risk Factors: How Can We Improve Outcomes in the High-Risk Patient?"; The American Journal of Medicine, 2007, 120(9A): S3-S9.

Haffner S M, entitled "Abdominal Adiposity and Cardiometabolic Risk: Do We Have All the Answers?", The American Journal of Medicine, 2007, 120(9A): S10-S17.

Mann K V et al., entitled "Management of acute iron overdose," Clinical Pharmacy, 1989, 8(6):428-440.

The Office Communication dated Dec. 2, 2010 for European Application No. 06839040.0.

Fernandez-Real, et al., "Cross-talk between iron metabolism and diabetes," Diabetes, 51 (2002), pp. 2348-2354.

Hershko et al., "A new synthetic oral chelator: evaluation in hypertransfused rats with selective radioiron probes of hepatocellular and reticuloendothelial iron stores and in iron-loaded rat heart cells in culture," Blood 97:4 (2001), pp. 1115-1122.

Communication pursuant to Article 94(3) EPC issued in connection with Application No. 05 754 177.3-2123 dated Jan. 21, 2011.

\* cited by examiner

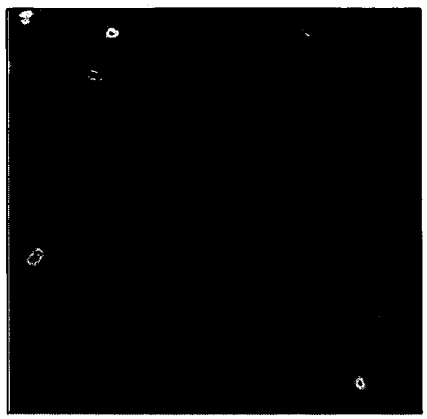
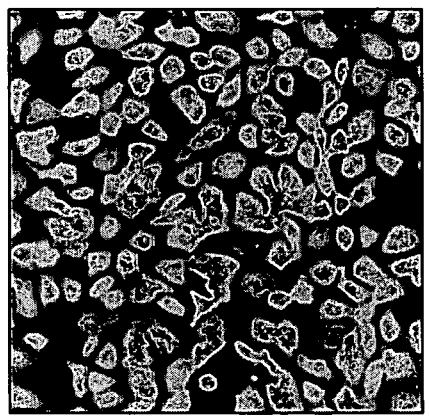
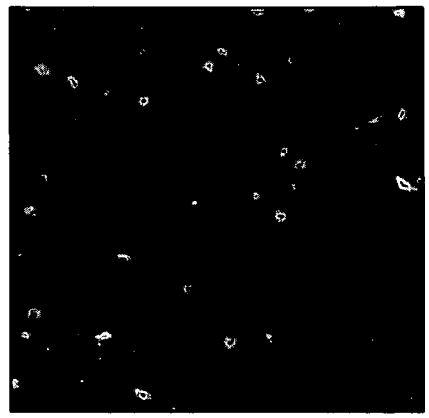
FIG. 23A  5mM GLUCOSE
FIG. 23B  30mM GLUCOSE
FIG. 23C  30mM GLUCOSE + DEFEROXAMINE

METHOD OF TREATING OR PREVENTING PATHOLOGIC EFFECTS OF ACUTE INCREASES IN HYPERGLYCEMIA AND/OR ACUTE INCREASES OF FREE FATTY ACID FLUX

This application claims the benefit of U.S. Provisional Patent Application Ser. No. 60/573,947, filed May 24, 2004.

FIELD OF THE INVENTION

The present invention relates to a method of treating or preventing pathologic effects of acute increases in hyperglycemia and/or acute increases of fatty acid flux in a subject.

BACKGROUND OF THE INVENTION

Cardiovascular Complications Associated with Diabetes are a Major Public Health Problem.

Diabetes mellitus is an epidemic in the United States (Brownlee, "Biochemistry and Molecular Cell Biology of Diabetic Complications," *Nature* 414:813-20 (2001); Nishikawa et al., "Normalizing Mitochondrial Superoxide Production Blocks Three Pathways of Hyperglycaemic Damage," *Nature* 404:787-90 (2000); Zimmet et al., "Global and Societal Implications of the Diabetes Epidemic," *Nature* 414: 782-7 (2001)). Currently 15-17 million adults (5% of the adult population) in the U.S. are affected by Type I and Type II diabetes (Harris et al., "Prevalence of Diabetes, Impaired Fasting Glucose, and Impaired Glucose Tolerance in U.S. Adults. The Third National Health and Nutrition Examination Survey, 1988-1994," *Diabetes Care* 21:518-24 (1998); AD Association, "Economic Costs of Diabetes in the U.S. in 2002," *Diabetes Care* 26:917-932 (2003)). By the year 2020, the diabetic population is expected to increase by another 44% (AD Association, "Economic Costs of Diabetes in the U.S. in 2002," *Diabetes Care* 26:917-932 (2003)). In addition to those with diabetes mellitus, an additional number of people display the metabolic syndrome, with impaired glucose and insulin tolerance and altered vascular reactivity.

The greatest impact of diabetes is on the vascular system (Caro et al., "Lifetime Costs of Complications Resulting From Type 2 Diabetes in the U.S. *Diabetes Care* 25:476-81 (2002)). Diabetic patients have an increased risk for vascular disease affecting the heart, brain, and peripheral vessels (Howard et al., "Prevention Conference VI: Diabetes and Cardiovascular Disease: Writing Group I: Epidemiology," *Circulation* 105:e132-7 (2002)). The relative risk of cardiovascular disease in diabetics is 2-8 times higher than age-matched controls (Howard et al., "Prevention Conference VI: Diabetes and Cardiovascular Disease: Writing Group I: Epidemiology," *Circulation* 105:e132-7 (2002)). Diabetes accounts for 180 billion dollars in annual health costs in the U.S., with 85% of this amount attributable to vascular complications (Caro et al., "Lifetime Costs of Complications Resulting From Type 2 Diabetes in the U.S. *Diabetes Care* 25:476-81 (2002)). Indeed, if macrovascular complications (stroke, MI, TIA, angina) and microvascular complications (nephropathy, neuropathy, retinopathy, wound healing) are considered together, the vast majority of diabetes related healthcare expenditures result from vasculopathies.

Diabetic Patients have Poor Outcomes because of Impaired Compensatory Vascular Growth.

The recognition that diabetes impairs survival after ischemic events dates back to the last century and has been independently confirmed by two landmark epidemiologic studies (The Framingham Study and The Diabetes Control and Complications Trial) (Garcia et al., "Morbidity and Mortality in Diabetics in the Framingham Population. Sixteen Year Follow-Up Study," *Diabetes* 23:105-11 (1974); TDCaCTR Group, "The Effect of Intensive Treatment of Diabetes on the Development and Progression of Long-Term Complications in Insulin-Dependent Diabetes Mellitus," *N Engl J Med* 329:977-86 (1993)). These prospective studies substantiated a relationship between poor glycemic control and decreased survival after myocardial infarction. Of note, these trials demonstrated that in addition to an increased incidence of ischemic episodes (Kannel et al., "Diabetes and Cardiovascular Risk Factors: the Framingham Study," *Circulation;* 59:8-13 (1979)), diabetic patients have higher rates of post-infarct complications, such as cardiac failure and secondary ischemic events (Hafffner et al., "Mortality From Coronary Heart Disease in Subjects With Type 2 Diabetes and in Nondiabetic Subjects With and Without Prior Myocardial Infarction," *N Engl J Med* 339:229-34 (1998); Zuanetti et al., "Influence of Diabetes on Mortality in Acute Myocardial Infarction: Data From the GISSI-2 Study," *J Am Coll Cardiol* 22:1788-94 (1993)). These disparities were not due to increased infarct size in the diabetic population (Wilson, "Diabetes Mellitus and Coronary Heart Disease," *Am J Kidney Dis* 32:S89-100 (1998)), suggesting that an impairment existed in the compensatory response of the diabetic myocardium. Similar impairments have been described in other diabetic tissues, including the extremities and brain (Uusitupa et al., "5-Year Incidence of Atherosclerotic Vascular Disease in Relation to General Risk Factors, Insulin Level, and Abnormalities in Lipoprotein Composition in Non-Insulin-Dependent Diabetic and Nondiabetic Subjects," *Circulation* 82:27-36 (1990); Jude et al., "Peripheral Arterial Disease in Diabetic and Nondiabetic Patients: a Comparison of Severity and Outcome," *Diabetes Care* 24:1433-7 (2001); Tuomilehto et al., "Diabetes Mellitus as a Risk Factor for Death From Stroke. Prospective Study of the Middle-Aged Finnish Population," *Stroke* 27:210-5 (1996)).

The concept that these impairments result from a poorly adapting diabetic vasculature has both clinical and experimental support. Since angiogenesis and collateral development are the processes that restore blood flow to watershed areas of the heart, the rapid restoration of a normal vascular density in the microvasculature ultimately determines patient outcome following ischemia (Helfant et al., "Functional Importance of the Human Coronary Collateral Circulation," *N Engl J Med* 284:1277-81 (1971); Chilian et al., "Microvascular Occlusions Promote Coronary Collateral Growth," *Am J Physiol* 258:H1103-11 (1990)). Indeed, the theoretical basis for therapeutic angiogenesis is the belief that augmenting the microvascular network in ischemic and watershed areas of the heart would be beneficial. Clinical as well as experimental studies provide conclusive evidence that diabetes impairs ischemia-driven neovascularization (Abaci et al., "Effect of Diabetes Mellitus on Formation of Coronary Collateral Vessels," *Circulation* 99:2239-42 (1999); Tooke, "Microvasculature in Diabetes," *Cardiovasc Res* 32:764-71 (1996); Waltenberger, "Impaired Collateral Vessel Development in Diabetes: Potential Cellular Mechanisms and Therapeutic Implications," *Cardiovasc Res* 49:554-60 (2001); Yarom et al., "Human Coronary Microvessels in Diabetes and Ischaemia. Morphometric Study of Autopsy Material," *J Pathol* 166:265-70 (1992)). In animal studies, diabetic animals demonstrate a decreased vascular density following hindlimb ischemia (Rivard et al., "Rescue of Diabetes-Related Impairment of Angiogenesis By Intramuscular Gene Therapy With Adeno-VEGF," *Am J Pathol* 154:355-63 (1999); Taniyama et al., "Therapeutic Angiogenesis Induced By Human Hepatocyte Growth Factor Gene in Rat Diabetic Hind Limb Ischemia Model: Molecular Mechanisms of Delayed Angiogenesis in Diabetes," *Circulation* 104:2344-50 (2001); Schatteman et al., "Blood-Derived Angioblasts Accelerate Blood-Flow Restoration in Diabetic Mice," *J Clin*

*Invest* 106:571-8 (2000)). Human angiographic studies have demonstrated that diabetic patients have fewer collateral vessels than non-diabetic controls (Abaci et al., "Effect of Diabetes Mellitus on Formation of Coronary Collateral Vessels," *Circulation* 99:2239-42 (1999)). Moreover, revascularization via coronary angioplasty, coronary artery bypass surgery, or lower extremity revascularization has a significantly lower success rate in diabetic patients even in the presence of a patient bypass conduit, suggesting the existence of a defect at the microcirculatory level (Kip et al., "Coronary Angioplasty in Diabetic Patients. The National Heart, Lung, and Blood Institute Percutaneous Transluminal Coronary Angioplasty Registry," *Circulation* 94:1818-25 (1996); Palumbo et al., "Diabetes Mellitus: Incidence, Prevalence, Survivorship, and Causes of Death in Rochester, Minn., 1945-1970," *Diabetes* 25:566-73 (1976); Schwartz et al., "Coronary Bypass Graft Patency in Patients With Diabetes in the Bypass Angioplasty Revascularization Investigation (BARI)," *Circulation* 106:2652-8 (2002); Kip et al., "Differential Influence of Diabetes Mellitus on Increased Jeopardized Myocardium After Initial Angioplasty or Bypass Surgery: Bypass Angioplasty Revascularization Investigation," *Circulation* 105:1914-20 (2002)).

TABLE 1

Published Studies Supporting Impaired Ischemic Responsiveness in Diabetes

| Study | Type of Study | Major Findings |
| --- | --- | --- |
| Abaci et al[a] | Clinical | Angiographic demonstration of decreased collaterals in the hearts of diabetic patients |
| Abbot et al[b] | Clinical | Cardiac failure is more common following an MI in diabetic patients |
| Altavilla et al[c] | Experimental | Diabetic mice have less VEGF, less angiogenesis and impaired wound healing compared to normal mice |
| Arora et al[d] | Clinical | Diabetics undergoing lower-extremity bypass maintain an impaired vascular reactivity even after successful surgical grafting, highlighting the limits of surgical interventions |
| Bradley et al[e] | Clinical | Diabetic patients have worse survival after an MI |
| Chou et al[f] | Experimental | First demonstration that myocardial tissue and cells from diabetic animals express less VEGF and its receptors |
| Frank et al[g] | Experimental | Diabetic mice express much less VEGF RNA and protein in their wounds |
| Goova et al[h] | Experimental | Blockade of the RAGE receptor accelerated wound healing, augmented VEGF expression, and increased angiogenesis in diabetic mice |
| Guzik et al[i] | Clinical | Blood vessels from diabetic patients produce augmented levels of superoxide, a marker/cause of oxidative stress |
| Haffner et al[j] | Clinical | Diabetic patients have a greatly increased incidence of experiencing an MI and dying from an MI |
| Hiller et al[k] | Clinical | Epidemiologic study suggesting that diabetic microangiopathy is greatly increased in diabetics |
| Jude et al[l] | Clinical | Diabetic patients have an increased incidence, severity, and poorer outcomes in peripheral arterial disease of the lower extremities |
| Kip et al[m] | Clinical | Angiographic and epidemiologic study demonstrating that diabetic patients have more diffuse atherosclerotic disease, and worse outcomes after seemingly successful interventional revascularization |
| Lerman et al[n] | Experimental | First demonstration that cells isolated from diabetic animals and patients produce attenuated levels of VEGF in hypoxia |
| Marsh et al[o] | Experimental | Monocytes from diabetic patients without retinopathy express less VEGF in hypoxia compared to monocytes from patients with diabetic retinopathy |
| Partamian et al[p] | Clinical | Diabetic patients have increased peri-infarct complications and decreased long-term survival |
| Rivard et al[q] | Experimental | Diabetes decreases reactive angiogenesis and tissue survival following hindlimb ischemia |
| Schatteman et al[r] | Experimental | Angioblasts from diabetic humans show decreased proliferation and differentiation so mature endothelial cells in culture. Also, diabetic mice have less tolerance to hindlimb ischemia than nondiabetic mice |
| Tepper et al[s] | Experimental | First demonstration that endothelial progenitor cells from diabetic patients show decreased function with assays that measure functions important for angiogenesis |
| Yarom et al[t] | Clinical | Autopsy pathologic study demonstrating that diabetic patients have decreased ischemia-induced reactive angiogenesis |

[a]Abaci et al., "Effect of Diabetes Mellitus on Formation of Coronary Collateral Vessels," Circulation 99: 2239-42 (1999)
[b]Abbott et al., "The Impact of Diabetes on Survival Following Myocardial Infarction in Men vs Women. The Framingham Study," Jama 260: 3456-60 (1988).
[c]Altavilla et al., "Inhibition of Lipid Peroxidation Restores Impaired Vascular Endothelial Growth Factor Expression and Stimulates Wound Healing and Angiogenesis in the Genetically Diabetic Mouse," Diabetes 50: 667-74 (2001).
[d]Arora et al., "Cutaneous Microcirculation in the Neuropathic Diabetic Foot Improves Significantly But Not Completely After Successful Lower Extremity Revascularization,". J Vasc Surg 35: 501-5 (2002).
[e]Bradley et al., "Survival of Diabetic Patients After Myocardial Infarction," Am J Med 20: 207-216 (1956).
[f]Chou et al., "Decreased Cardiac Expression of Vascular Endothelial Growth Factor and its Receptors in Insulin-Resistant and Diabetic States: A Possible Explanation for Impaired Collateral Formation in Cardiac Tissue," Circulation 105: 373-9 (2002).
[g]Frank et al., "Regulation of Vascular Endothelial Growth Factor Expression in Cultured Keratinocytes. Implications for Normal and Impaired Wound Healing," J Biol Chem 270: 12607-13 (1995).
[h]Goova et al., "Blockade of Receptor for Advanced Glycation End-Products Restores Effective Wound Healing in Diabetic Mice," Am J Pathol 159: 513-25 (2001).
[i]Guzik et al., "Mechanisms of Increased Vascular Superoxide Production in Human Diabetes Mellitus: Role of AND(P)H Oxidase and Endothelial Nitric Oxide Synthase," Circulation 105: 1656-62 (2002).
[j]Haffner et al., "Mortality From Coronary Heart Disease in Subjects With Type 2 Diabetes and in Nondiabetic Subjects With and Without Prior Myocardial Infarction," N Engl J Med 339: 229-34 (1998).
[k]Hiller et al., "Diabetic Retinopathy and Cardiovascular Disease in Type II Diabetics. The Framingham Heart Study and the Framingham Eye Study," Am J Epidemiol 128: 402-9 (1988).
[l]Jude et al., "Peripheral Arterial Disease in Diabetic and Nondiabetic Patients: a Comparison of Severity and Outcome," Diabetes Care 24: 1433-7 (2001).
[m]Kip et al., "Coronary Angioplasty in Diabetic Patients. The National Heart, Lung, and Blood Institute Percutaneous Transluminal Coronary Angioplasty Registry," Circulation 94: 1818-25 (1996)
[n]Lerman et al., "Cellular Dysfunction in the Diabetic Fibroblast: Impairment in Migration, Vascular Endothelial Growth Factor Production, and Response to Hypoxia," Am J Pathol 162: 303-12 (2003).
[o]Marsh et al., "Hypoxic Induction of Vascular Endothelial Growth Factor is Markedly Decreased in Diabetic Individuals Who Do Not Develop Retinopathy," Diabetes Care 23: 1375-80 (2000).
[p]Partamian et al., "Acute Myocardial Infarction in 258 Cases of Diabetes. Immediate Mortality and Five-Year Survival," N Engl J Med 273: 455-61 (1965).
[q]Rivard et al., "Rescue of Diabetes-Related Impairment of Angiogenesis By Intramuscular Gene Therapy With Adeno-VEGF," Am J Pathol 154: 355-63 (1999)
[r]Schatteman et al., "Blood-Derived Angioblasts Accelerate Blood-Flow Restoration in Diabetic Mice," J Clin Invest 106: 571-8 (2000).
[s]Tepper et al., "Human Endothelial Progenitor Cells From Type II Diabetics Exhibit Impaired Proliferation, Adhesion, and Incorporation Into Vascular Structures," Circulation 106: 2781-6 (2002).
[t]Yarom et al., "Human Coronary Microvessels in Diabetes and Ischaemia. Morphometric Study of Autopsy Material," J Pathol 166: 265-70 (1992).

Despite the preponderance of these observations, the mechanisms underlying impaired neovascularization in diabetes remain unclear. Impaired VEGF expression has been implicated as a significant contributing factor (Rivard et al., "Rescue of Diabetes-Related Impairment of Angiogenesis By Intramuscular Gene Therapy With Adeno-VEGF," *Am J Pathol* 154:355-63 (1999); Schratzberger, et al., "Reversal of Experimental Diabetic Neuropathy by VEGF Gene Transfer," *J Clin Invest* 107:1083-92 (2001); Aiello et al., "Role of Vascular Endothelial Growth Factor in Diabetic Vascular Complications," *Kidney Int Suppl* 77:S113-9 (2000)). A detailed understanding of the mechanism of reduced VEGF expression would provide a useful framework for new approaches to improve diabetic outcomes following ischemic events.

Ischemia-Induced Neovascularization Occurs by Two Mechanisms: Angiogenesis and Vasculogenesis.

After the appropriate hypoxic signaling cascade is initiated, compensatory vascular growth in response to ischemic insult occurs by two different mechanisms (FIG. 1). In angiogenesis, mature resident endothelial cells proliferate and sprout new vessels from an existing vessel in response to an angiogenic stimulus. In a more recently described mechanism, termed vasculogenesis, circulating cells with characteristics of vascular stem cells (endothelial progenitor cells, or EPCs) are mobilized from the bone marrow in response to an ischemic event, and then home specifically to ischemic vascular beds and contribute to neovascularization (Asahara et al., "Isolation of Putative Progenitor Endothelial Cells for Angiogenesis," *Science* 275:964-7 (1997); Shi et al., "Evidence for Circulating Bone Marrow-Derived Endothelial Cells," *Blood* 92:362-7 (1998); Asahara et al., "Bone Marrow Origin of Endothelial Progenitor Cells Responsible for Postnatal Vasculogenesis in Physiological and Pathological Neovascularization," *Circ Res* 85:221-8 (1999); Isner et al., "Angiogenesis and Vasculogenesis as Therapeutic Strategies for Postnatal Neovascularization," *J Clin Invest* 103:1231-6 (1999); Crosby et al., "Endothelial Cells of Hematopoietic Origin Make a Significant Contribution to Adult Blood Vessel Formation," *Circ Res* 87:728-30 (2000); Pelosi et al., "Identification of the Hemangioblast in Postnatal Life," *Blood* 100:3203-8 (2002)).

Hypoxia-Inducible Factor-1 (HIF-1) is the Central Mediator of the Hypoxia Response Including Subsequent Blood Vessel Growth.

The observation that ischemia regulates blood vessel growth has been known for many years, yet the responsible factor eluded identification until 1992, when Semenza and colleagues described a hypoxia-responsive transcription factor (HIF-1) which mediates erythropoietin gene upregulation (Semenza et al., "A Nuclear Factor Induced by Hypoxia via de Novo Protein Synthesis Binds to the Human Erythropoietin Gene Enhancer at a Site Required for Transcriptional Activation," *Mol Cell Biol* 12:5447-54 (1992); Semenza et al., "Hypoxia-Inducible Nuclear Factors Bind to an Enhancer Element Located 3' to the Human Erythropoietin Gene," *Proc Natl Acad Sci USA* 88:5680-4 (1991)). HIF-1 proved to be a novel transcription factor conserved in all metazoan phyla and is ubiquitously present in all cells examined thus far (Carmeliet et al., "Abnormal Blood Vessel Development and Lethality in Embryos Lacking a Single VEGF Allele," *Nature* 380:435-9 (1996)). Evidence for its involvement in angiogenesis stemmed from the initial observation that VEGF was strongly upregulated by hypoxic conditions (Shweiki et al., "Vascular Endothelial Growth Factor Induced by Hypoxia May Mediate Hypoxia-Initiated Angiogenesis," *Nature* 359:843-5 (1992)). Soon thereafter, HIF-1 was shown to be the transcription factor responsible for VEGF upregulation by hypoxia and hypoglycemia (Forsythe et al., "Activation of Vascular Endothelial Growth Factor Gene Transcription by Hypoxia-Inducible Factor 1," *Mol Cell Biol* 16:4604-13 (1996)). It is now clear that HIF-regulated VEGF expression is essential for vascular development during both embryogenesis and postnatal neovascularization in physiologic and pathologic states (Carmeliet et al., "Abnormal Blood Vessel Development and Lethality in Embryos Lacking a Single VEGF Allele," *Nature* 380:435-9 (1996); Carmeliet et al., "Abnormal Blood Vessel Development and Lethality in Embryos Lacking a Single VEGF Allele," *Nature* 380:435-9 (1996); Iyer et al., "Cellular and Developmental Control of O2 Homeostasis by Hypoxia-Inducible Factor 1 Alpha," *Genes Dev* 12:149-62 (1998)). HIF-1 consists of the oxygen-regulated HIF-1α subunit and the HIF-1β subunit, which is not regulated by oxygen. HIF-1 is now believed to be the master transcription factor directing the physiologic response to hypoxia by upregulating pathways essential for adaptation to ischemia, including angiogenesis, vasculogenesis, erythropoiesis and glucose metabolism (FIG. 2).

Regulation of HIF-1α Transcriptional Activation.

The HIF-1 transcriptional complex is comprised of HIF-1α/β and more than seven other factors that modulate gene transcription. The two predominant functional components of this complex are HIF-1α and CBP/p300, which directly interact to transactivate gene expression. HIF-1α function is predominantly regulated by oxygen via protein stabilization and post-translational modification. Recent reports demonstrate that HIF-1α is activated by phosphorylation in vitro, enhancing HIF-mediated gene expression (Richard et al., "p42/p44 Mitogen-Activated Protein Kinases Phosphorylate Hypoxia-Inducible Factor 1alpha (HIF-1alpha) and Enhance the Transcriptional activity of HIF-1," *J Biol Chem* 274: 32631-7 (1999)). Whether this modification results in a direct stimulation of the transactivation function of HIF-1α itself or facilitates recruitment of co-activators is not clear (Richard et al., "p42/p44 Mitogen-Activated Protein Kinases Phosphorylate Hypoxia-Inducible Factor 1alpha (HIF-1alpha) and Enhance the Transcriptional activity of HIF-1," *J Biol Chem* 274:32631-7 (1999); Sang et al., "Signaling Up-Regulates the Activity of Hypoxia-Inducible Factors by Its Effects on p300," *J Biol Chem* 278:14013-9 (2003)).

It has also been recently demonstrated that CBP/p300 also undergoes phosphorylation in vitro, enhancing its ability to function as a transcriptional activator in association with HIF-1α (Sang et al., "Signaling Up-Regulates the Activity of Hypoxia-Inducible Factors by Its Effects on p300," *J Biol Chem* 278:14013-9 (2003)). Thus, cellular states that promote phosphorylation of these two factors likely increase hypoxia-induced gene expression, while those that favor dephosphorylation have the opposite effect. Although HIF-1 mediated gene expression is essential for both angiogenesis and vasculogenesis, the role of its regulation in diabetic states has not been previously examined.

Both Angiogenesis and Vasculogenesis are Modulated by VEGF.

It is well known that angiogenesis is mediated by VEGF and this mechanism has been extensively investigated (Ferrara et al., "The Biology of VEGF and its Receptors," *Nat Med* 9:669-76 (2003)). Recently, VEGF has also been implicated in regulation of vasculogenesis (FIG. 2). Ischemia is a potent mobilizer of endothelial progenitor cells from the bone marrow. This appears to be mediated through VEGF signaling, as EPCs express both VEGF receptor 1 and 2 on their cell surface (Asahara et al., "VEGF Contributes to Postnatal Neovascularization by Mobilizing Bone Marrow-Derived Endothelial Progenitor Cells," *Embo J* 18:3964-72 (1999); Takahashi et al., "Ischemia- and Cytokine-Induced Mobilization of Bone Marrow-Derived Endothelial Progenitor Cells for Neovascularization," *Nat Med* 5:434-8 (1999); Kalka et al., "Vascular Endothelial Growth Factor(165) Gene Transfer Augments Circulating Endothelial Progenitor Cells in Human Subjects," *Circ Res* 86:1198-202 (2000); Gill et al., "Vascular Trauma Induces Rapid but Transient Mobilization of VEGFR2(+)AC133(+) Endothelial Precursor Cells," *Circ Res* 88:167-74 (2001); Hattori et al., "Vascular Endothelial Growth Factor and Angiopoietin-1 Stimulate Postnatal Hematopoiesis by Recruitment of Vasculogenic and Hematopoietic Stem Cells," *J Exp Med* 193:1005-14 (2001)). Given that VEGF production is impaired in diabetes mellitus, it seems likely that various aspects of vasculogenesis, including EPC mobilization, may also be impaired. Indeed, recent evidence has demonstrated that the incorporation of these vascular progenitors into blood vessels is decreased in diabetic states.

VEGF Expression May be Regulated in a Tissue-Specific Manner.

It also clear that various tissues and organs in diabetic patients exhibit different pathologies. The retina is often characterized by excessive angiogenesis, while skin, muscle, and nerves in diabetic patients suffer from a paucity of new vessel formation. Similarily, diabetic retinopathy has been characterized by increased levels of ocular VEGF levels, (Aiello et al., "Vascular Endothelial Growth Factor in Ocular Fluid of Patients with Diabetic Retinopathy and Other Retinal Disorders," *N Engl J Med* 331:1480-7 (1994); Adamis et al., "Increased Vascular Endothelial Growth Factor Levels in the Vitreous of Eyes with Proliferative Diabetic Retinopathy," *Am J Ophthalmol* 118:445-50 (1994)), while impaired wound healing has been characterized by severely decreased levels of VEGF (Frank et al., "Regulation of Vascular Endothelial Growth Factor Expression in Cultured Keratinocytes. Implications for Normal and Impaired Wound Healing," *J Biol Chem* 270:12607-13 (1995); Peters et al., "Vascular Endothelial Growth Factor Receptor Expression During Embryogenesis and Tissue Repair Suggests a Role in Endothelial Differentiation and Blood Vessel Growth," *Proc Natl Acad Sci USA* 90:8915-9 (1993); Silhi, N., "Diabetes and Wound Healing," *J Wound Care* 7:47-51 (1998); Brown, L. F., "Expression of Vascular Permeability Factor (Vascular Endothelial Growth Factor) by Epidermal Keratinocytes During Wound Healing," *J Exp Med* 176:1375-9 (1992); Nissen et al., "Vascular Endothelial Growth Factor Mediates Angiogenic Activity During the Proliferative Phase of Wound Healing," *Am J Pathol* 152:1445-52 (1998)). This so-called "diabetic paradox," by which the diabetic phenotype exhibits both excessive and impaired new blood vessel formation in different tissues, leads to different types of complications. It is believed this phenomenon represents a cell- and tissue-specific difference in the transcriptional regulation of VEGF.

Hyperglycemia Results in Specific Impairments of Cellular Function through Overproduction of Reactive Oxygen Species: a Potential Link to VEGF.

The cellular mechanism that accounts for impaired hypoxia-induced VEGF and SDF-1 expression has not yet been determined. Recently, the biochemical basis for hyperglycemia-induced cellular damage was described, demonstrating that many of the effects of high glucose are mediated through four specific cellular pathways (FIG. 3) (Brownlee, "Biochemistry and Molecular Cell Biology of Diabetic Complications," *Nature* 414:813-20 (2001); Nishikawa et al., "Normalizing Mitochondrial Superoxide Production Blocks Three Pathways of Hyperglycaemic Damage," *Nature* 404: 787-90 (2000)). Intracellular elevations in glucose increase flux of metabolites through glycolysis and the Kreb's cycle, resulting in overproduction of ROS by the mitochondria. Overproduction of ROS inhibits GAPDH activity, resulting in accumulation of early glucose metabolites in the initial phases of glycolysis. The abundance of these metabolites and their inability to progress through glycolysis causes shunting of these intermediates into alternative pathways of glucose utilization (polyol pathway, hexosamine pathway, protein kinase C pathway, and AGE pathway, FIG. 3). Accumulation of end products in each of these pathways leads to specific changes in cellular function, including gene expression (Nissen et al., "Vascular Endothelial Growth Factor Mediates Angiogenic Activity During the Proliferative Phase of Wound Healing," *Am J Pathol* 152:1445-52 (1998)), and are implicated in the pathophysiology of diabetic complications (Brownlee, "Biochemistry and Molecular Cell Biology of Diabetic Complications," *Nature* 414:813-20 (2001)). Indeed, specific blockade of one, several, or all of these pathways has been shown to prevent diabetic complications in an animal model, including those complications that result from ischemic injury (Hammes et al., "Benfotiamine Blocks Three Major Pathways of Hyperglycemic Damage and Prevents Experimental Diabetic Retinopathy," *Nat Med* 9:294-9 (2003); Obrosova et al., "Aldose Reductase Inhibitor Fidarestat Prevents Retinal Oxidative Stress and Vascular Endothelial Growth Factor Overexpression in Streptozotocin-Diabetic Rats," *Diabetes* 52:864-71 (2003)).

Hyperglycemia-induced reactive oxygen species impair the ability of HIF-1α to mediate appropriate upregulation of VEGF and the chemokine SDF-1 that are required for neovascularization in ischemic settings. This impairment also affects hypoxia-specific functions of vascular effector cells. This results in impaired angiogenesis, vasculogenesis, and diminished tissue survival in diabetic states.

The present invention is directed to treating or preventing the pathologic sequelae of acute hyperglycemia and/or increased fatty acid flux in a subject, thus, preventing metabolite-induced reactive oxygen-species mediated injury.

SUMMARY OF THE INVENTION

One aspect of the present invention relates to a method of treating or preventing pathologic sequelae of acute hyperglycemia and/or increased fatty acid flux in non-diabetic subjects, metabolic syndrome/insulin resistance subjects, impaired fasting glucose subjects, impaired glucose tolerance subjects, and diabetic subjects. This method involves administering an ROS inhibitor to the subject under conditions effective to treat or prevent pathologic sequelae of acute hyperglycemia and/or increased fatty acid flux in the subject.

Another aspect of the present invention relates to a method of promoting neovascularization in a subject prone to hyperglycemia or increased fatty acid flux. This method involves administering an ROS inhibitor to the subject under conditions effective to promote neovascularization in the subject.

A further aspect of the present invention pertains to a method of inhibiting oxidation or excessive release of free fatty acids in a subject. This method involves administering to the subject certain compounds under conditions effective to inhibit excessive release of free fatty acids in the subject. These compounds include thiazolidinedione, nicotinic acid, etomoxir, and ranolazine.

A further aspect of the present invention is directed to a method of identifying compounds suitable for treatment or prevention of ROS-mediated injury. This method involves providing a diabetic animal model and inducing diabetes in the animal model. A compound to be tested is then administered to the animal model. Compounds which achieve recovery of local oxygen tension, blood flow, increase in vessel density, and tissue survival in the animal model as therapeutic candidates for treating or preventing ROS-mediated injury are then recovered.

The present invention provides a means of restoring deficient angiogenesis in response to ischemia in patients with disorders of glucose and fatty acid metabolism. This would drastically reduce the rate of lower limb amputation, and reduce the extent of cardiac and brain damage due to heart attacks and strokes. In addition, it would result in healing of intractable diabetic foot ulcers, a major clinical problem for which there is currently no available effective medical treatment.

BRIEF DESCRIPTION OF THE DRAWINGS

FIGS. 23A-C show the free intracellular iron measurement in bovine aortic endothelial cells after incubation with 5 mM or 30 mM glucose (FIGS. 23A and 23B, respectively) or 30 mM glucose plus 100 μM deferoxamine (FIG. 23C) for 24 hours. Detection of free iron was accomplished by visualizing the fluorescent marker fura-2 AM.

FIGS. 30A-B show oxygenation levels in non-diabetic and diabetic mice, respectively. P1-P4 on the y-axis designate adjacent quadrants of the ischemic skin flap starting closest to the site of attachment to the animal, i.e. P1, and proceeding distally to P4. FIGS. 30C-D show mobilization of bone marrow-derived endothelial cells in response to ischemia. Flk-1 on the y-axis is a marker for ischemic bone-marrow-derived endothelial precursor cells. CD11b on the x-axis is a general marker for bone marrow-derived endothelial precursor cells. FIGS. 30E-F show the amount of capillary formation in non-diabetic and diabetic mice, respectively. NI on the y-axis represents capillary density of a non-ischemic control. Area C on the y-axis represents the capillary density in an ischemic skin flap after 7 days.

DETAILED DESCRIPTION OF THE INVENTION

Figure 1:
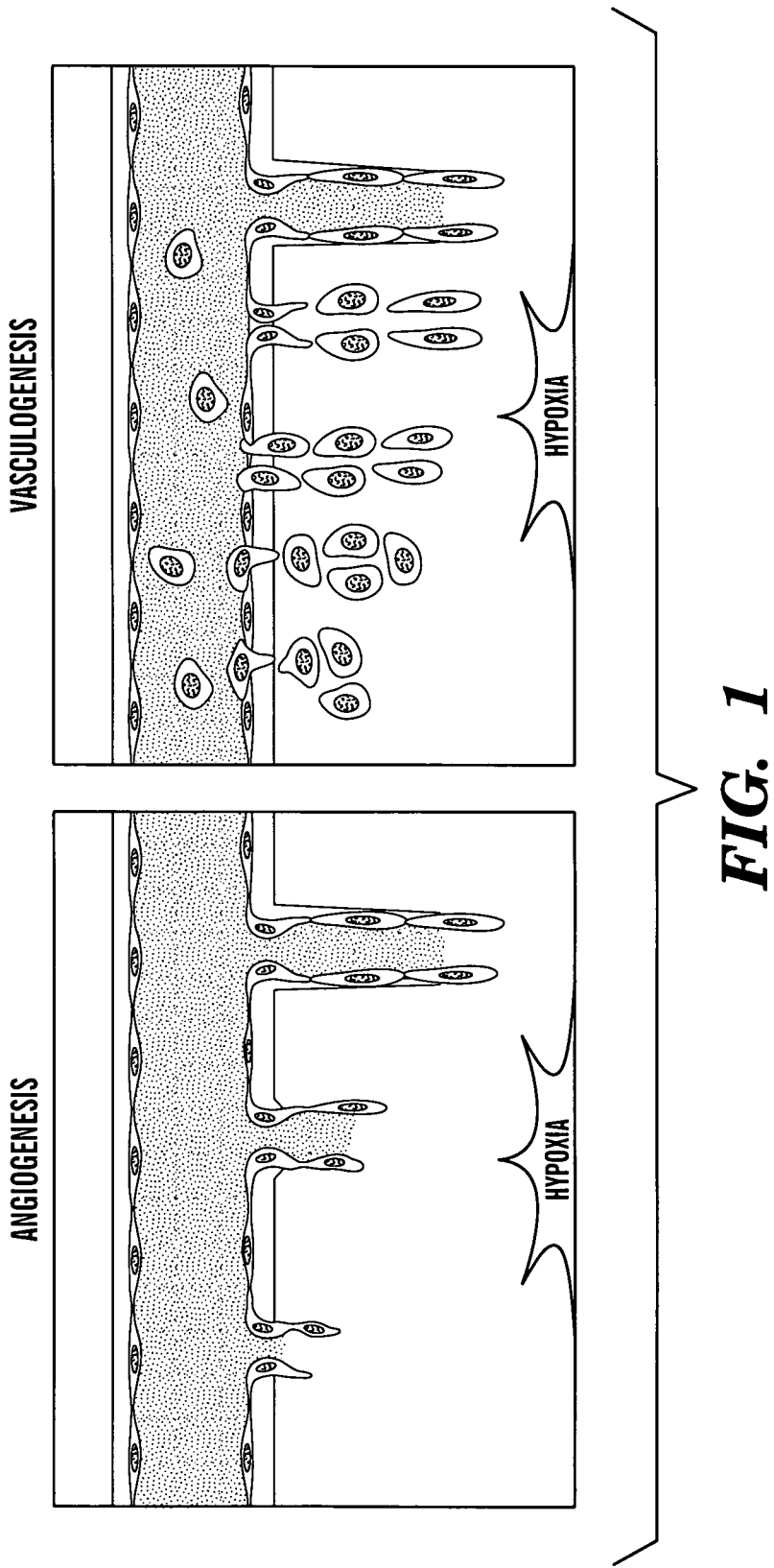
FIG. 1 shows a schematic of angiogenesis and vasculogenesis.
Figure 2:
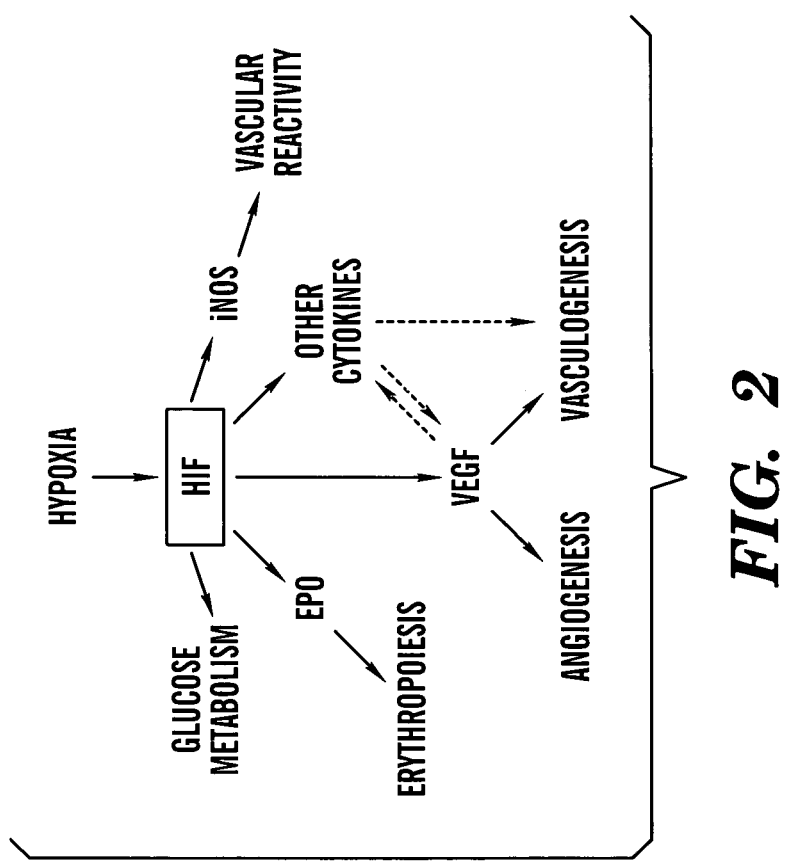
FIG. 2 shows the central role of HIF and VEGF in the ischemic response.
Figure 3:
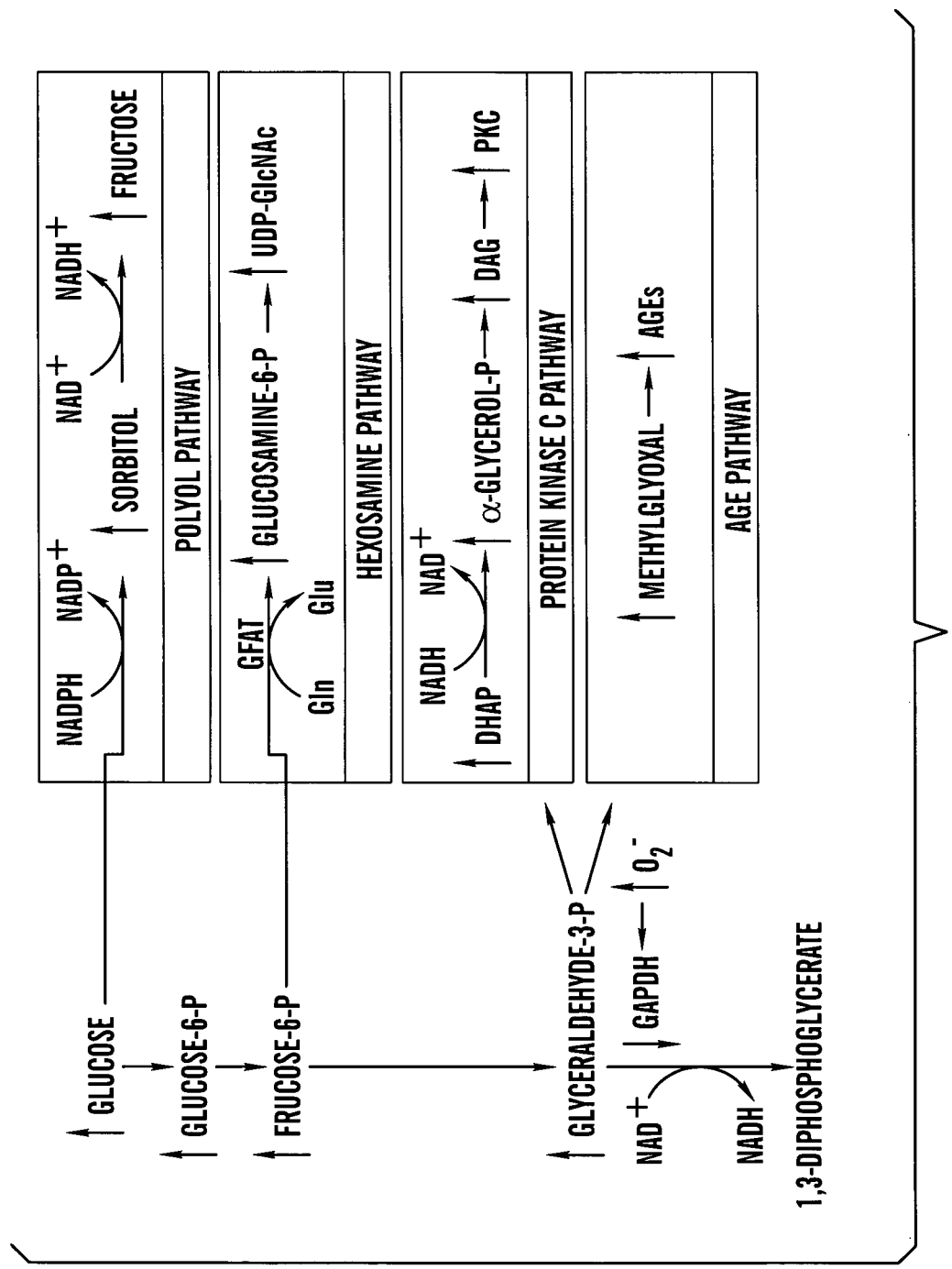
FIG. 3 shows pathways of hyperglycemic damage.
Figure 4:
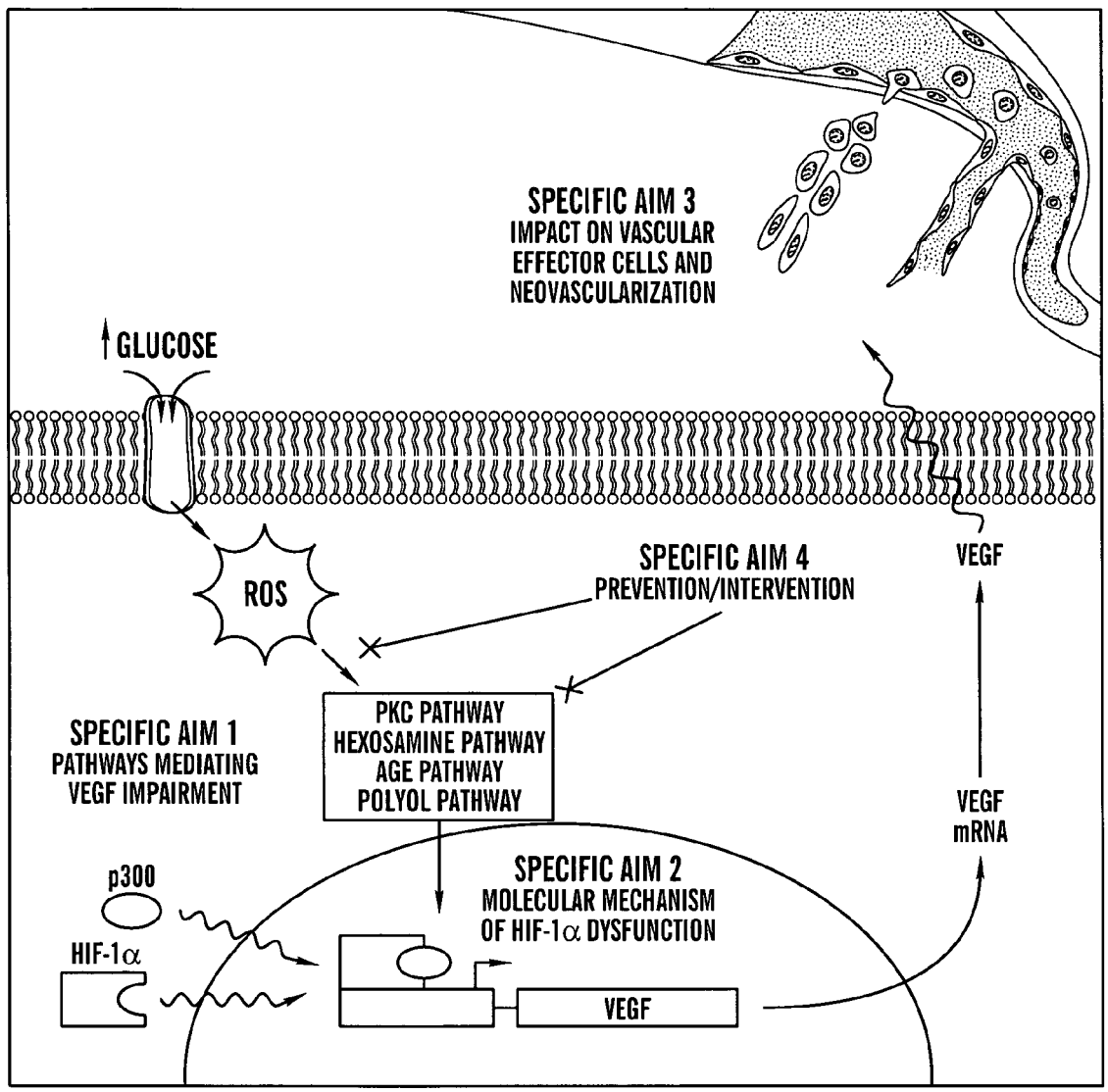
FIG. 4 shows an overall experimental plan.

One aspect of the present invention relates to a method of treating or preventing pathologic effects of acute increases in hyperglycemia and/or acute increases of fatty acid flux in non-diabetic subjects, metabolic syndrome/insulin resistance subjects, impaired fasting glucose subjects, impaired glucose tolerance subjects, and diabetic subjects. This method involves administering an ROS inhibitor to the subject under conditions effective to treat or prevent pathologic effects of acute increases in hyperglycemia and/or acute increases in fatty acid flux in the subject.

As noted above, in this aspect of the present invention, the claimed method can be applied to non-diabetic subjects, metabolic syndrome/insulin resistance subjects, impaired fasting glucose subjects, impaired glucose tolerance subjects, and diabetic subjects. In each case, the subject has a base line level of hyperglycemia and/or fatty acid flux. The present invention is directed to the prevention or treatment of pathologic conditions in subjects whose base line levels of hyperglycemia and/or fatty acid flux undergo a rapid and relatively short-term (i.e. acute) increase.

Subjects where acute increases in hyperglycemia and/or acute increases of fatty acid flux take place may be suffering from any of the following conditions: diabetes-specific microvascular pathology in the retina (i.e. diabetic retinopathy), renal glomerulus (i.e. diabetic nephropathy), peripheral nerve (i.e. diabetic neuropathy), accelerated atherosclerotic macrovascular disease affecting arteries that supply the heart, brain, and lower extremities (i.e. diabetic macrovasular disease), or nonalcoholic fatty liver disease ("NAFLD") which includes a wide spectrum of liver injury ranging from simple steatosis to steatohepatitis ("NASH"), fibrosis, and cirrhosis. The pathologic effect of acute increases in hyperglycemia and/or acute increases of fatty acid flux may also be prevented or treated where the subject has a critical care illness, an acute myocardial infarction, an acute stroke, or who has undergone arterial bypass or general surgery.

Acute increases in hyperglycemia and/or acute increases of fatty acid flux impairs mobilization of vascular endothelial cell precursors from the bone marrow. This may take the form of impairing mobilization of vascular endothelial cell precursors from the bone marrow, impairing HIF-1α- and SDF-1-mediated upregulation of vascular endothelial growth fact, and/or ROS-mediated injury which inhibits neovascularization. The subject can also have an ischemic condition which includes coronary artery disease, peripheral vascular disease, cerebral vascular disease, non-healing foot ulcers, or a wound (acute or chronic).

The ROS inhibitor can be alpha lipoic acid, a superoxide dismutase mimetic, or a catalase mimetic. The superoxide dismutase mimetic or the catalase mimetic can be MnTBAP (Mn(III)tetrakis(4-benzoic acid)porphyrin chloride)(produced by Calbiochem), ZnTBAP (Zn(III)tetrakis(4-benzoic acid)porphyrin chloride), SC-55858 (manganese (II) dichloro (2R,3R,8R,9R-bis-cyclohexano-1,4,7,10,13-pentaazacyclopentadecane)] Euk-134 (3,3'-methoxysalenMn (III))(produced by Eukarion), M40403 (dichloro [(4aR,13aR, 17aR,21aR)-1,2,3,4,4a,5,6,12,13,13a,14,15,16,17,17a,18, 19,20,21-eicosahydro-11,7-nitrilo-7H-dibenzo[1,4,7,10] tetraazacycloheptadecine-kappaN$^5$,kappaN$^{13}$,kappaN$^{18}$, kappaN$^{21}$,kappaN$^{22}$] manganese) (produced by Metaphore), AEOL 10112, AEOL 10113, and AEOL 10150 (manganese (III) mesotetrakis(di-N-ethylimidazole)porphyrin)(all AEOL compounds being produced by Incara Pharmaceuticals). Alternatively, the ROS inhibitor can be an iron chelator. Of the iron chelators, deferoxamine or DFO may be the most important, because it is FDA-approved for treatment of iron excess in thallasemia. In addition, the ROS inhibitor can be a composition comprised of a mixture of iron chelators.

When deferoxamine is employed, a patient (e.g., a patient with an acute myocardial infarction) can be treated with intramuscular injections of 1,000 to 10,000 mg of deferoxamine or with intravenous injections of 100 to 10,000 mg of deferoxamine. Such patients can be treated within 24 hours of symptoms by intravenous injection of deferoxamine in liquid form at a concentration between 100 to 10,000 mg/liter of deferoxamine. Deferoxamine can also be administered together with DFP, ICL-670, a poly (ADP-ribose) polymerase inhibitor, and a glucagon-like peptide-1 fragment that prevents hyperglycemia-induced ROS production, for example, GLP-1 (9-37 amide), and GLP-9-37). Alternatively, deferoxamine can be administered together with a poly (ADP-ribose) polymerase inhibitor including, but not limited to, nicotinamide, 3-aminobenzamide, PJ34 (N-(6-oxo-5,6-dihydrophenanthridin-2-yl)-N,N-dimethylacetamide), and mixtures thereof.

While deferoxamine can provide life-saving treatment for patients in iron overload situations, numerous deferoxamine derivatives can also be employed. Aliphatic, aromatic, succinic, and methylsulphonic analogs of DFO have been synthesized to enhance the lipophilicity of DFO (Ihnat et al., "Solution Equilibria of Deferoxamine Amides," *J. Pharm Sci.* 91:1733-1741 (2002), which is hereby incorporated by reference in its entirety). Specifically, these derivatives include formamide-deferoxamine, acetamide-deferoxamine, propylamide deferoxamine, butylamide-deferoxamine, benzoylamide-deferoxamine, succinamide-derferoxamine, and methylsulfonamide-deferoxamine. Hydroxyethyl starch (HES)-deferoxamine has been synthesized which was shown to have a greater plasma half-life than deferoxamine (Pedchenko et al., "Desferrioxamine Suppresses Experimental Allergic Encephalomyelitis Induced by MBP in SJL mice," *J. Neuroimmunol.* 84:188-197 (1998), which is hereby incorporated by reference in its entirety). An aminooxyacetyl-ferrioxamine has also been prepared allowing for site specific conjugation to antibodies (Pochon et al., "A Novel Derivative of the Chelon Desferrioxamine for Site-specific Conjugation to Antibodies," *Int. J. Cancer.* 43:1188-1194 (1989), which is hereby incorporated by reference in its entirety). Fluorescent deferoxamine derivatives have also been synthesized for free iron measurements in a range of biological experimental conditions (A1-Mehdi et al., "Depolarization-associated iron release with abrupt reduction in pulmonary endothelial shear stress in situ," *Antioxid. Redox Signal.* 2:335-345 (2000), which is hereby incorporated by reference in its entirety).

Other suitable iron chelators include those set forth in Table 2:

| | | PHARMACOLOGY | | | |
|---|---|---|---|---|---|
| Name | Formula | Chem. structure | MW | Dent | Route |
| DFO | 4-[3,5-bis-[hydroxyphenyl]-1,2,4-triazol-1-yl]-benzoic acid | *(structure)* | 560 | 6 | parenteral |
| HBED | N,N'-bis(o-hydroxybenzyl)ethylenediamine-N,N'-diacetic acid | *(structure)* | 388 | 6 | oral/parenteral |
| PIH | pyridoxal isanicotinoyl hydrazone | *(structure)* | 262 | 3 | oral |
| DFT | 4'-hydroxy-(S)-desaza desmethyl-desfemithiocin; (S)-4,5-dihydro-2-(2,4-dihydroxyphenyl)-4-thiazofecarboxylic acid | *(structure)* | 238 | 3 | oral |
| DFP (L1) | 1,2-dimethyl-3-hydroxypyridin-4-one | *(structure)* | 139 | 2 | oral |

PHARMACOLOGY

| Name | Formula | Chem. structure | MW | Dent | Route |
|---|---|---|---|---|---|
| S-DFO | hydroxyethyl-starch-bound-deferoxamine | — | 250.000 | 6 | i.v. |
| ICL-670 | 4-[3,5-bis-(hydroxyphenyl)-1,2,4-triazol-1-yl]-benzoic acid | (structure) | 373 | 3 | oral |
| GT56-252 | 4,5-dihydro-2-(2,4-dihyroxiphenyl)-4-methylthiazole-4(S)-carboxylic acid | (structure) | 252 | 3 | oral |

HEBED is a synthetic chelator that appears to have higher efficacy than DFO, and fewer adverse effects. However, in primate studies, it still had to be administered by subcutaneous infusion (Chaston, et. al., "Iron Chelators for the Treatment of Iron Overload Disease: Relationship Between Structure, Redox Activity, and Toxicity" *Am J Hematol.* 73:200-210 (2003), which is hereby incorporated by reference in its entirety.

PIH is an orally active, triedentate chelator which crosses membranes much better than does DFO. PCIH (i.e. analogues of 2-pyridylcarboxaldehyde isonicotinoyl hydrazone) compounds (which are not shown in Table 2) are substantially similar to PIH. This class of chelators can also access mitochondrial iron pools, making it a potential drug for the rare genetic disease Friedrich's Ataxia (caused by a mutation in the mitochondrial iron-sulfur complex chaperone frataxin).

Like HBED, DFT and GT56-252 are both second generation hydroxypyridones that are in preclinical or phase I trials.

DFP or Deferipone, is approved for clinical use in Europe under the trade name Ferriprox. It is a bidentate chelator that is administered orally. However, the efficacy and toxicity of the drug are still controversial. Combined use of DFO and DFP has been proposed.

S-DFO is a starch-bound DFO derivative that has a longer half-life after intravenous administration.

ICL-670 is a tridentate chelator of the triazole family currently in phase III trials. It is orally available and is administered once a day (Hershko, C., et al., *Blood* 97:1115-1122 (2001), which is hereby incorporated by reference in its entirety).

Another class of iron chelator is the biomimetic class (Meijler, M M, et al. "Synthesis and Evaluation of Iron Chelators with Masked Hydrophilic Moieties" *J. Amer. Chem. Soc.* 124:1266-1267(2002), which is hereby incorporated by reference in its entirety). These molecules are modified analogues of such naturally produced chelators as DFO and ferrichrome. The analogues allow attachment of lipophilic moieties (e.g., acetoxymethyl ester) which greatly enhance passage through membranes. The lipophilic moieties are then cleaved intracellularly by endogenous esterases, converting the chelators back into hydrophilic molecules which cannot leak out of the cell. These compounds appear to be highly effective, and reduce free-iron mediated oxidative damage much more efficiently than does DFO.

Lastly, a number of compounds developed as inhibitors of advanced glycation endproduct (AGE) formation and/or degradation and tested in animal models of diabetic complications appear to act via chelation (Price, D L, et al., *JBC* 276:48967-72 (2001), which is hereby incorporated by reference in its entirety). These include (in order from weakest to strongest copper chelation): aminoguanidine and pyridoxamine; carnosine, phenazinediamine, OPB-9195, and tenilsetam. The so-called AGE-breakers, phenacylthiazoloum and phenacyldimethythiazolium bromide, and their hydrolysis products, were among the most potent inhibitors of copper-catalyzed autoxidation of ascorbate. Aminoguanidine has been through Phase II/III trials, pyridoxamine has been through Phase II trials, and the AGE breakers are currently in Pase II trials.

The ROS generation by hyperglycemia or increased fatty acid flux takes place in the mitochondria; however, applicants believe that its transmission within the cell is mediated by iron released by superoxide-initiated oxidation of iron-containing proteins in the mitochondria. This iron is known to be capable of generating damaging hydroxy radicals and superoxides by what is called "Fenton Chemistry". To distinguish between the iron(II) and iron(III) combinations, the convention is to use Fenton-like reagent for the $Fe^{3+}/H_2O_2$ mixture and restrict the use of Fenton's reagent to denote the $Fe^{2+}/H_2O_2$ mixture. The Fenton-like reagent is also capable of oxidizing organic substrates, but it is somewhat less reactive than Fenton's reagent. As iron(III) can be produced in applications of Fenton's reagent, Fenton chemistry and Fenton-like chemistry often occur simultaneously. Thus, it is really an ROS inhibitor, rather than an inhibitor of fatty acid flux or oxidation.

The inhibitors can be administered orally, parenterally, transdermally, subcutaneously, intravenously, intramuscularly, intraperitoneally, by intraversal instillation, intracularly, intranasally, intraarterially, intralesionally, or by application to mucous membranes, such as that of the nose, throat, and bronchial tubes. The inhibitors can be administered alone or with a pharmaceutically acceptable salt, carrier, excipient, or stabilizer, and can be in solid or liquid form, including, for example, tablets, capsules, powders, solutions, suspensions, or emulsions.

The solid unit dosage forms can be of the conventional type. The solid form can be a capsule, such as an ordinary gelatin type containing the inhibitors of the present invention and a carrier, for example, lubricants and inert fillers such as lactose, sucrose, or cornstarch. In another embodiment, the inhibitors are tableted with conventional tablet bases such as lactose, sucrose, or cornstarch in combination with binders like acacia, cornstarch, or gelatin, disintegrating agents such as, cornstarch, potato starch, or alginic acid, and a lubricant like stearic acid or magnesium stearate.

In another aspect, the inhibitors of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, the inhibitors of the present invention may be incorporated with excipients and used in the form of tablets, capsules, elixirs, suspensions, syrups, and the like. In one aspect, such formulations should contain at least 0.1% of the inhibitors of the present invention. The percentage of the inhibitors in the formulations of the present invention may, of course, be varied and may conveniently be between about 2% to about 60% of the weight of the unit. The amount of inhibitors in the formulations of the present invention is such that a suitable dosage will be obtained. As one example, formulations according to the present invention are prepared so that an oral dosage unit contains between about 1 and 250 mg of the inhibitors.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

As described above, in one aspect of the present invention, the formulations containing the inhibitors may be administered parenterally. Solutions or suspensions of the inhibitors can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

When the inhibitor is deferoxamine, deferoxamine compositions for parental use can be in the form of a solution or a suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as benzyl alcohol or methyl parabens, or antioxidants such a sodium bisulfite. Buffers such as acetates, citrates, or phosphates and agents for the adjustment of tonicity such as sodium chloride or dextrose may also be added. The parenteral preparation can be enclosed in ampules, disposable syringes, or multiple dose vials made of glass or plastic.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

Slow-release deferoxamine compositions for intramuscular administration may be formulated by standard methods, such as a microcrystalline composition. Deferoxamine preparations with longer half-lives may be formulated by conjugation of deferoxamine with, for example, dextrans or polyethylene glycols. In addition, deferoxamine derivatives with great ability to permeate cell membranes can be made by linking deferoxamine to a lipophilic ester moiety such as acetyoxymethyl ester, which is then removed by intracellular esterases once the compound is inside the cell (Meijler et al., "Synthesis and Evaluation of Iron Chelators with Masked Hydrophilic Moieties", *J. Am. Chem. Soc.* 124:12666-12667 (2002)).

The formulations containing the inhibitors of the present invention may also be administered directly to the airways in the form of an aerosol. For use as aerosols, the inhibitors of the present invention in solution or suspension may be packaged in a pressurized aerosol container together with suitable propellants, for example, hydrocarbon propellants like propane, butane, or isobutane with conventional adjuvants. The inhibitors of the present invention also may be administered in a non-pressurized form such as in a nebulizer or atomizer.

In carrying out this method, an ROS-mediated injury can be treated or prevented. Hyperglycemic conditions which can be so treated or prevented include chronic hyperglycemia. This includes hyperglycemic diabetes or acute hyperglycemia (such as stress hyperglycemia). Resistance to insulin is another form of a metabolite-induced excessive ROS production in accordance with this aspect of the present invention. This can be where there is resistance to insulin resulting in increased free fatty acid flux and increased free fatty acid oxidation by vascular cells.

Another aspect of the present invention relates to a method of promoting neovascularization in a subject prone to hyperglycemia or increased fatty acid flux. This method involves administering an ROS inhibitor to the subject under conditions effective to promote neovascularization in the subject.

Here, neovasularization can be in response to hypoxic signaling, and involve both angiogenesis (e.g. cardiac or lower limb) or vasculogenesis. The subject can have an ischemic condition, such as coronary artery disease, peripheral vascular disease, cerebral vascular disease, or a wound which is either chronic or acute.

The ROS inhibitor, its formulation, and its modes of administration for this embodiment of the present invention are the same as those described above.

Here the subject is preferably a human prone to hyperglycemia or fatty acid flux.

A further aspect of the present invention pertains to a method inhibiting oxidation or excessive release of free fatty acids in a subject. This method involves administering to the subject certain compounds under conditions effective to inhibit oxidation excessive release of free fatty acids in the subject. These compounds include thiazolidinedione, nicotinic acid, etomoxir, and ranolazine.

In this embodiment of the present invention, the above-identified compounds are formulated and administered in substantially the same way as noted above.

In this aspect of the present invention, the subject is a mammal, preferably a human.

A further aspect of the present invention is directed to a method of identifying compounds suitable for treatment or prevention of ROS-mediated injury. This method involves providing a diabetic animal model and inducing diabetes in the animal model. A compound to be tested is then administered to the animal model. Compounds which achieve recovery of local oxygen tension, blood flow increase in vessel dentity, and tissue survival in the animal model as therapeutic candidates for treating or preventing ROS-mediated injury are then recovered.

EXAMPLES

Example 1

Three Different Murine Models of Diabetes Exhibit Increased Tissue Necrosis in Response to Ischemia It is well recognized that diabetic tissues have a reduced tolerance to ischemia (Haffner et al., "Mortality From Coronary Heart Disease in Subjects With Type 2 Diabetes and in Nondiabetic Subjects With and Without Prior Myocardial Infarction," *N Engl J Med* 339:229-34 (1998); Jude et al., "Peripheral Arterial Disease in Diabetic and Nondiabetic Patients: a Comparison of Severity and Outcome," *Diabetes Care* 24:1433-7 (2001); Tuomilehto et al., "Diabetes Mellitus as a Risk Factor for Death From Stroke. Prospective Study of the Middle-Aged Finnish Population," *Stroke* 27:210-5 (1996); Waltenberger, "Impaired Collateral Vessel Development in Diabetes: Potential Cellular Mechanisms and Therapeutic Implications," *Cardiovasc Res* 49:554-60 (2001); Rivard et al., "Rescue of Diabetes-Related Impairment of Angiogenesis By Intramuscular Gene Therapy With Adeno-VEGF," *Am J Pathol* 154:355-63 (1999); Kip et al., "Differential Influence of Diabetes Mellitus on Increased Jeopardized Myocardium After Initial Angioplasty or Bypass Surgery: Bypass Angioplasty Revascularization Investigation," *Circulation* 105:1914-20 (2002); Partamian et al., "Acute Myocardial Infarction in 258 Cases of Diabetes. Immediate Mortality and Five-Year Survival," *N Engl J Med* 273:455-61 (1965); Simovic et al., "Improvement in Chronic Ischemic Neuropathy After Intramuscular phVEGF165 Gene Transfer in Patients With Critical Limb Ischemia," *Arch Neurol* 58:761-8 (2001); Margolis et al., "Risk Factors for Delayed Healing of Neuropathic Diabetic Foot Ulcers: A Pooled Analysis," *Arch Dermatol* 136:1531-5 (2000), which are hereby incorporated by reference in their entirety). Clinically, this results in increased rates of heart failure, increased mortality and prolonged wound healing. While this relationship has been studied in animal models of cardiac and hind-limb ischemia (Rivard et al., "Rescue of Diabetes-Related Impairment of Angiogenesis By Intramuscular Gene Therapy With Adeno-VEGF," *Am J Pathol* 154:355-63 (1999); Schratzberger, et al., "Reversal of Experimental Diabetic Neuropathy by VEGF Gene Transfer," *J Clin Invest* 107:1083-92 (2001), which are hereby incorporated by reference in their entirety), there are limitations to these models. Due to the variations in large vessel anatomy, the resultant pattern of necrosis is unpredicatable, leading to discrepancies in the experimental results. In addition, it is not possible to determine tissue survival except at sacrifice. Furthermore, indirect measures of perfusion such as laser doppler must often be utilized to estimate ischemia, but these techniques do not provide direct information regarding tissue oxygenation.

Figure 5:
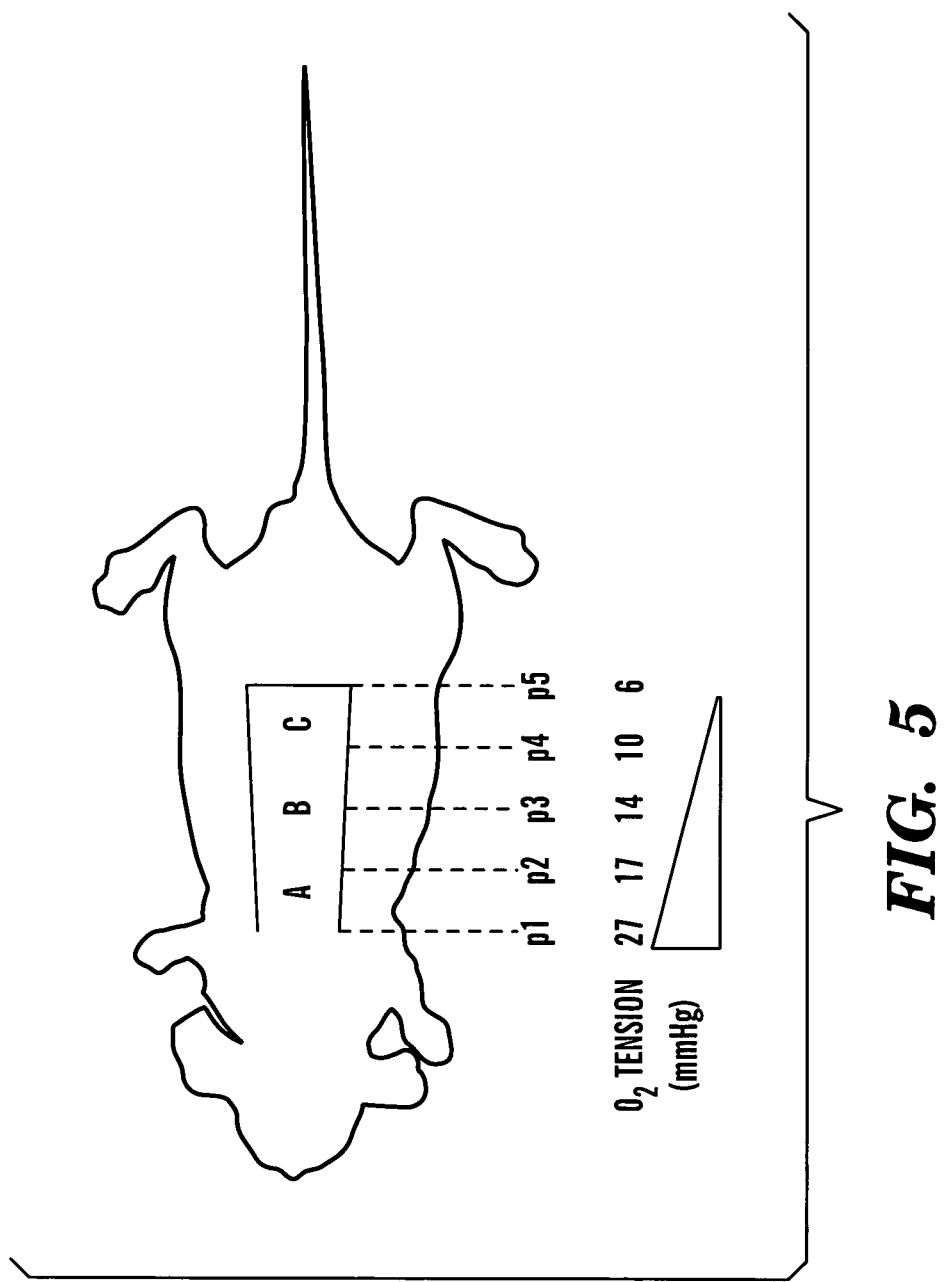
FIG. 5 shows a murine model of graded cutaneous ischemia. Regions A, B, and C reflect increasingly ischemic tissue regions, as measured by direct tissue oxygen tension at reference points p1 (27 mm Hg)-p5 (6 mm Hg).

To address these problems, a novel model of graded ischemia in the dorsal soft tissue of mice has been created (FIG. 5) (Tepper et al., "Human Endothelial Progenitor Cells From Type II Diabetics Exhibit Impaired Proliferation, Adhesion, and Incorporation Into Vascular Structures," *Circulation* 106:2781-6 (2002), which is hereby incorporated by reference in its entirety). Since the vascular anatomy of the mouse dorsum is precisely known, and the major axial vessels can be easily visualized, one can create a reliable zone of ischemia with a reproducible oxygen gradient in the tissue. This has been confirmed with direct tissue oxygen tension measurements utilizing five reference points (p1-p5) spaced 0.5 cm apart proceeding from the least to most ischemic regions. This also allows for the study of discrete microenvironments of ischemia (Areas A, B, C), with Area A being the least ischemic and Area C being the most ischemic portion of the soft tissue. The design of this model facilitates direct dynamic measurement of oxygen tension, quantitation of tissue survival, with a degree of reproducibility that allows correlation of specific oxygen tensions with changes in gene expression.

Figure 6:
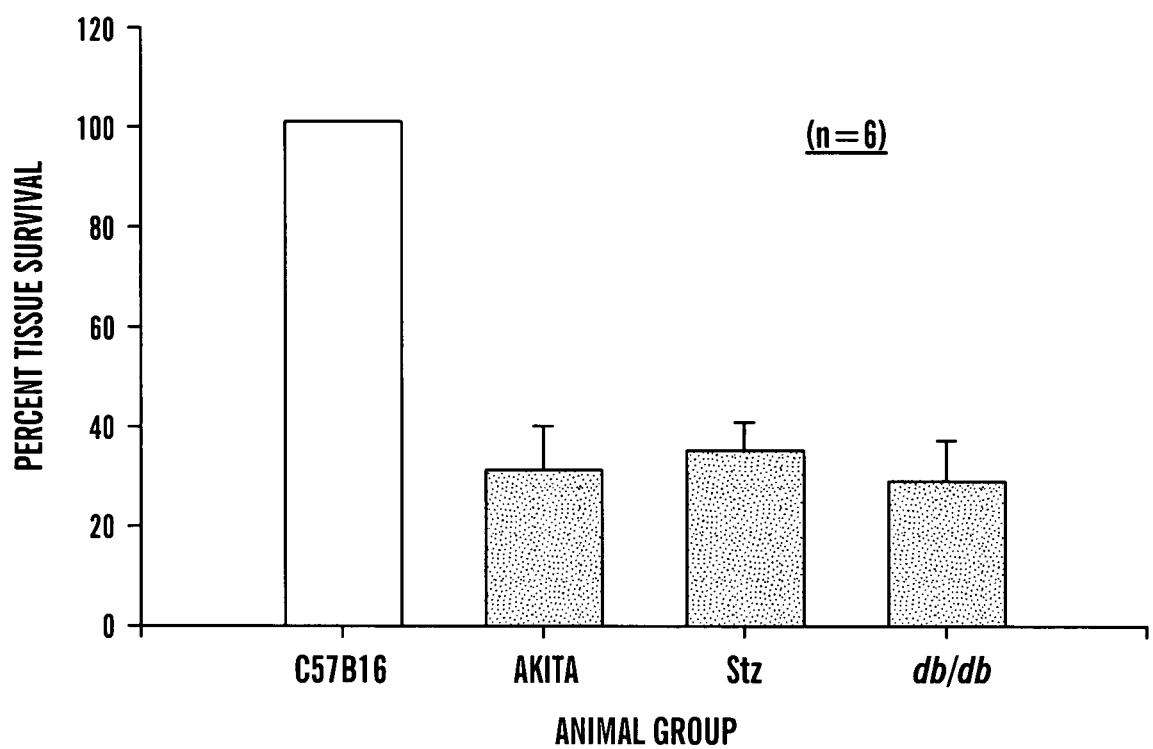
FIG. 6 shows tissue survival in diabetic mice.

Using this model, it has been observed that the response to ischemia is dramatically impaired in three different murine models of diabetes, all characterized by significant hyperglycemia. In the db/db mouse, a leptin receptor deficient model of Type II diabetes, it has been demonstrated that ischemia produces significant necrosis of nearly all of the tissue, whereas all the tissue survived in non-diabetic animals. Similar results were noted in the streptozotocin-induced diabetic mouse model (Stz), as well as an Akita mouse model of Type I diabetes with tissue survival approximately 30% of that observed in non-diabetic mice (FIG. 6). Importantly, oxygen tensions and vascular density (as determined by CD31 staining and FITC-lectin perfusion) were identical in all four groups prior to surgery, suggesting that the differences in tissue survival were due to an impaired response to ischemia rather than baseline differences in vascular density.

Example 2

Diabetic Mice have a Diminished Neovascular Response to Ischemia

Figure 7:
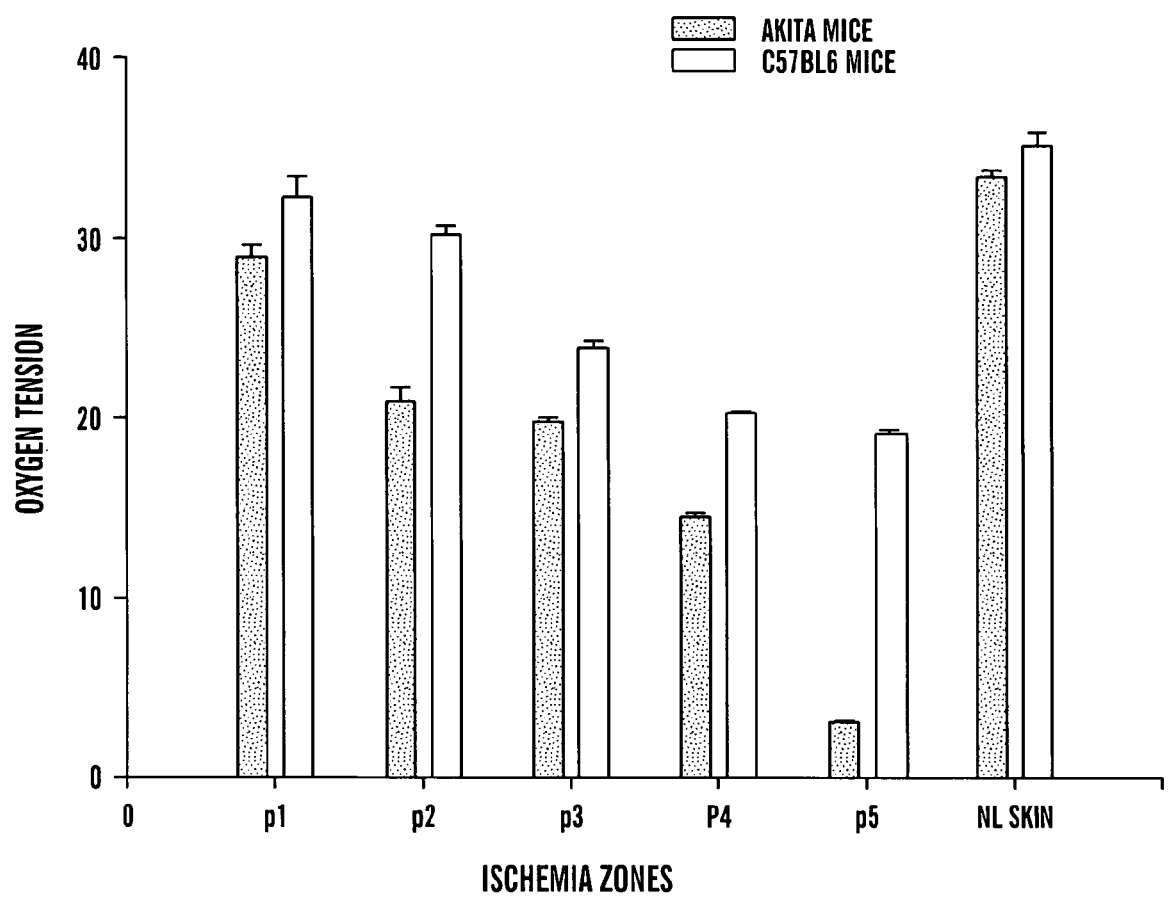
FIG. 7 shows oxygen tension measurements in ischemic tissue from least ischemic (p1) to most ischemic (p5) compared to normal skin oxygen tension (NL Skin).
Figure 8:
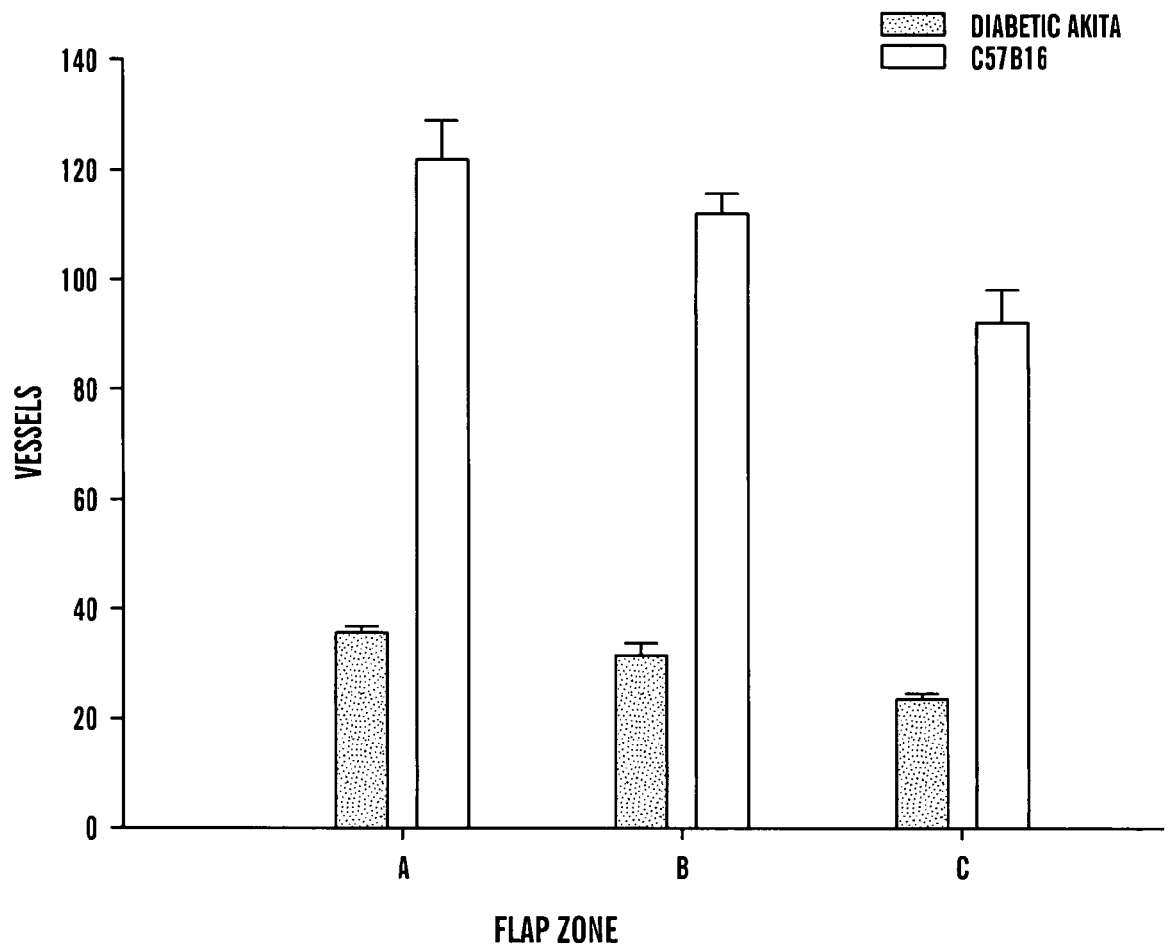
FIG. 8 shows the number of blood vessels identified by CD31 staining in areas A, B, and C of ischemic flaps.

The decrease in tissue survival observed in this model was also associated with diminished neo-vascularization in the surviving tissue. Seven days following surgery, the oxygen tension in ischemic soft tissue of non-diabetic mice approaches that of normal skin (FIG. 7, grey plot), while the diabetic mice demonstrate a significant reduction in oxygen tension at the same reference points (black plot). These findings correlated with a reduction in the number of blood vessels observed in the surviving tissue in diabetic mice (FIG. 8, black plot) as determined by CD31 staining. This suggests that ischemia-induced neovascularization is impaired in diabetic mice.

Example 3

Figure 9:
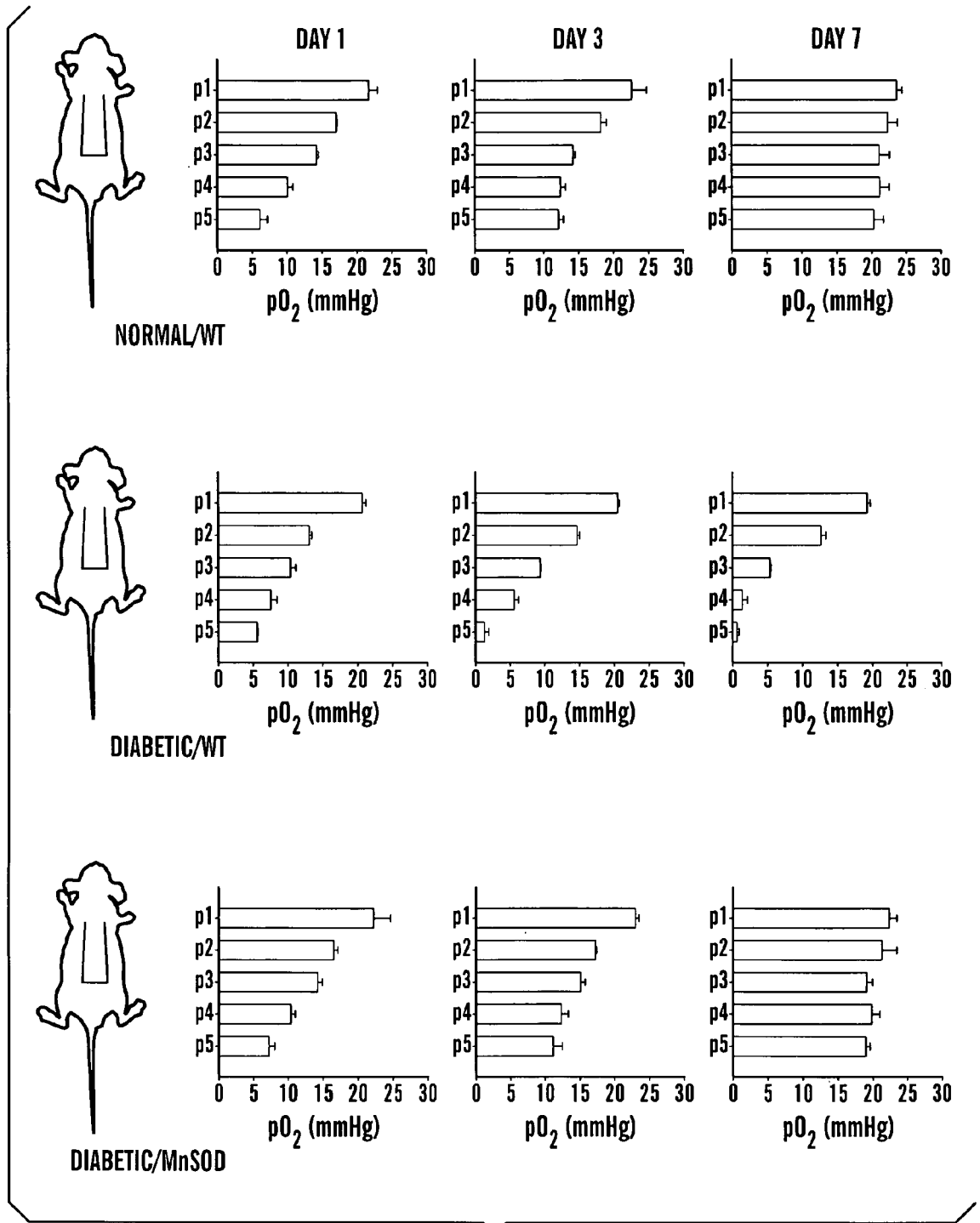
FIG. 9 shows oxygen tension measurements post-operatively in wild type and MnSOD transgenic mice with streptozotocin-induced diabetes.

Prevention of Hyperglycemia-Induced Reactive Oxygen Species Restores Tissue Survival in a Diabetic Animal Model It has been examined whether increased oxidative damage was an upstream modulator of the impaired tissue response to ischemia in diabetic animals. To address this question, a transgenic mouse that overexpress mitochondrial manganese superoxide dismutase (MnSOD) was used. MnSOD catalyzes the formation of molecular oxygen from superoxide, preventing the generation of ROS, and effectively blocks all four pathways of hyperglycemic damage. Diabetes was induced in wild type and MnSOD transgenic mice via streptozotocin injection, and hyperglycemia (>400 mg/dl) was maintained for one month. Following ischemic surgery, tissue was monitored by direct oxygen tension measurements on days 1, 3, and 7. Compared to wild type diabetic mice, MnSOD diabetic mice demonstrated a rapid recovery of local tissue oxygen tensions, neovascularization, and increased tissue survival that was similar to that observed in non-diabetic mice (FIG. 9). Non-diabetic MnSOD control mice were similar to wild type mice. This suggests that the prevention of hyperglycemia-induced ROS improves tissue survival in diabetic animals following ischemic events.

Example 4

Figure 10:
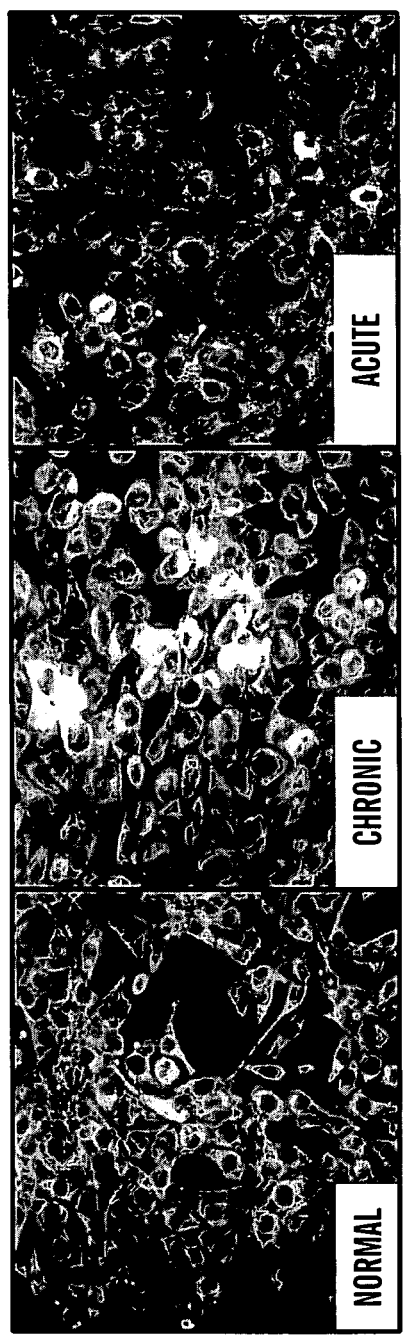
FIG. 10 shows JC-1 staining of C2C12 myoblasts cultivated in normal glucose (5 mM), as well as acute and chronic high glucose (25 mM).

Chronic High Glucose Levels also Correlate with Increased Mitochondrial Membrane Potential The effects of high glucose culture on mitochondrial membrane potential were also examined in C2C12 cells exposed to acute or chronic high glucose using the potential-dependent cationic dye JC-1. This has been used as an indicator of oxidative stress. In concordance with recent reports (Du et al., "Hyperglycemia Inhibits Endothelial Nitric Oxide Synthase Activity by Posttranslational Modification at the Akt Site," *J Clin Invest* 108:1341-8 (2001), which is hereby incorporated by reference in its entirety), chronic high glucose profoundly increases the mitochondrial proton electrochemical gradient (evidenced by a shift to orange-red fluorescence) compared to normal glucose culture or acute exposure to high glucose (FIG. 10) (Du et al., "Hyperglycemia Inhibits Endothelial Nitric Oxide Synthase Activity by Posttranslational Modification at the Akt Site," *J Clin Invest* 108:1341-8 (2001), which is hereby incorporated by reference in its entirety). Thus, a correlation exists between hyperglycemia, oxidative stress, and VEGF impairment in vitro.

Example 5

Impaired VEGF Production Lies at the Level of RNA Transcription

Figure 11:
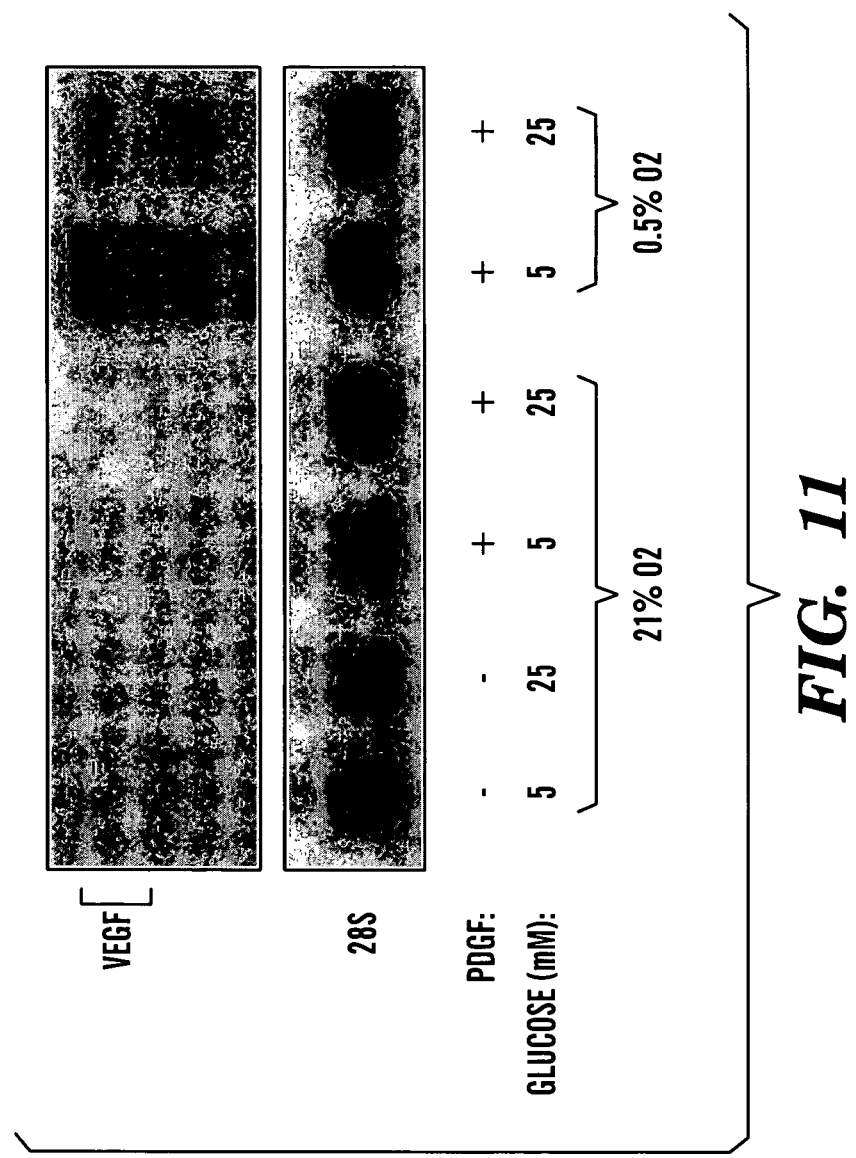
FIG. 11 shows VEGF mRNA in high and low glucose in response to hypoxia.
Figure 12:
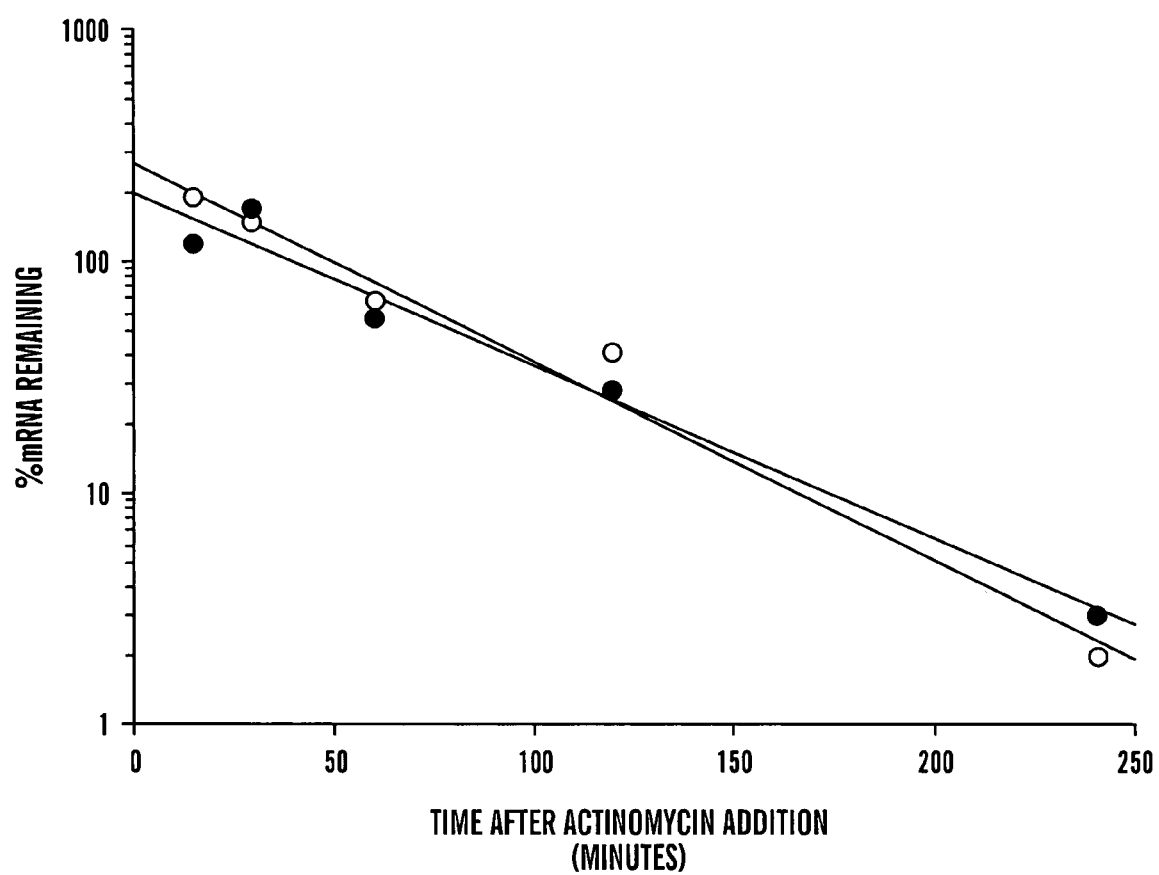
FIG. 12 shows VEGF mRNA half life in cells cultivated in normal glucose (●) or high glucose (○) conditions.
Figure 13:
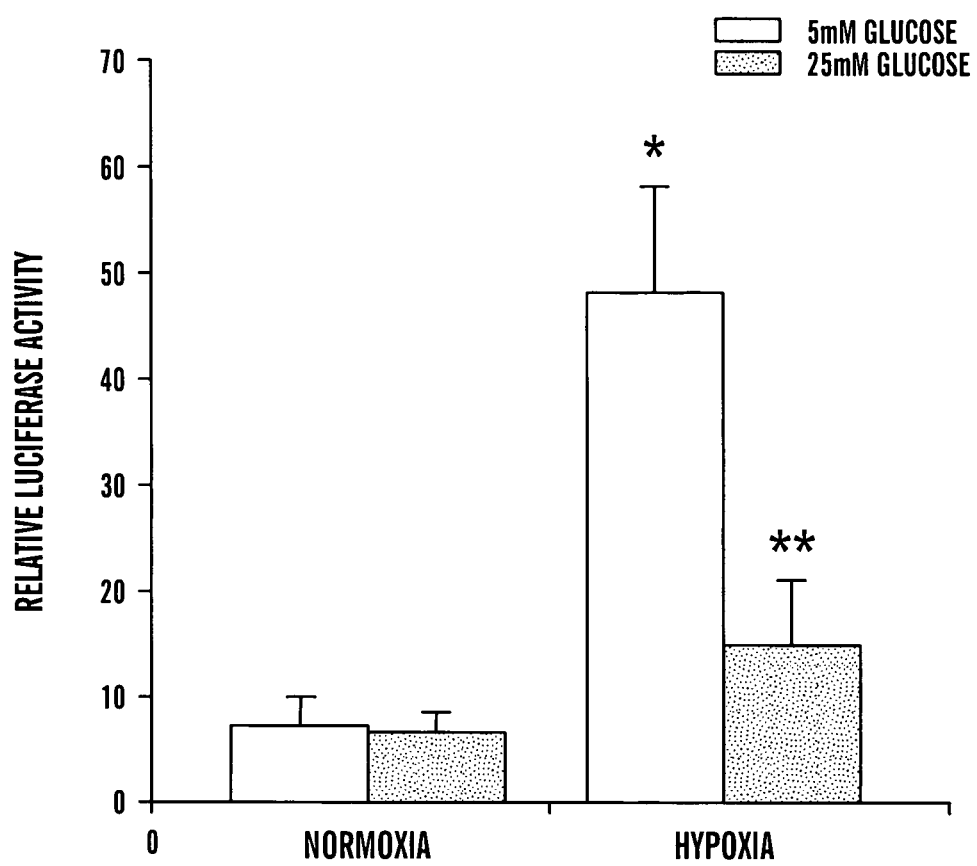
FIG. 13 shows VEGF promoter activity in C2C12 myoblasts in normal (5 mM, grey) and high glucose (25 mM, black) after hypoxic stimulus.

With evidence implicating decreased VEGF production as a contributor to impaired angiogenesis in hyperglycemic states, the mechanism by which high glucose alters VEGF expression was examined. Analysis of VEGF mRNA transcripts present in normal and high glucose culture under hypoxic conditions revealed a substantial reduction in VEGF mRNA production in cells cultivated in high glucose (FIG. 11). Possible explanations for this finding included abnormal mRNA stabilization or decreased promoter activity in high glucose. To address the issue of mRNA stabilization, the RNA ½-life in C2C12 myoblasts was examined by inhibiting transcription with actinomycin D. Results of these experiments showed no differences in VEGF mRNA stability between normal and hyperglycemic cells despite significant differences in VEGF protein levels (FIG. 12). VEGF promoter activity was then examined using a reporter construct containing the full length VEGF promoter fused to a luciferase gene. This construct was transiently co-transfected into C2C12 myoblasts cultivated in normal and high glucose with a constitutively expressed Renilla plasmid to control for transfection efficiency. Hypoxia-induced luciferase production was significantly impaired in high glucose conditions compared to normal glucose controls (FIG. 13). This demonstrates that the impaired VEGF protein production in hypoxia resulted from decreased VEGF transcription in vivo.

Figure 14:
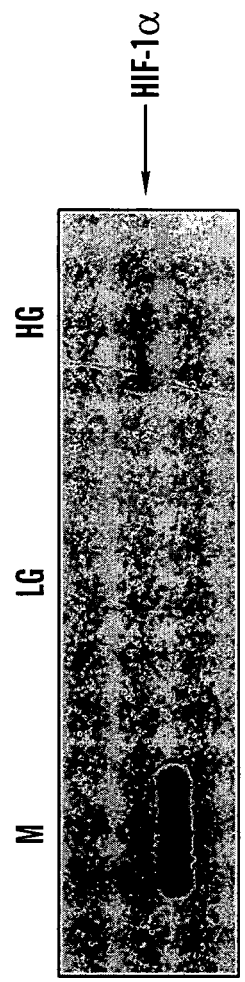
FIG. 14 shows HIF-1α is preferentially glycosylated in high glucose conditions (HG, 25 mM) compared to normal glucose (NG, 5 mM).

Example 6 p300 and HIF-1α are Substrates for O-linked Glycosylation, Potentially Linking the Hexosamine Pathway of Hyperglycemic Oxidative Damage to Impairements in Hypoxia-Induced VEGF Expression Based on findings implicating impaired HIF-1α transactivation in high glucose as the mechanism for impaired hypoxia-induced VEGF expression, potential post-translational modifications of HIF-1α were examined under these conditions. It was initially examined whether HIF-1α is a substrate for O-linked glycosylation. HIF-1α was immunoprecipitated from cells grown in normal or high glucose conditions, and Western blots were probed with an antibody that specifically recognizes residues containing the O-linked glycosylation modification. While no glycosylated HIF-1α was present under normal glucose conditions, there was significant glycosylation in high glucose (FIG. 14). This is the first demonstration that HIF-1α is a substrate for O-linked glycosylation, and is preferentially glycosylated under conditions of high glucose.

Figure 15A:
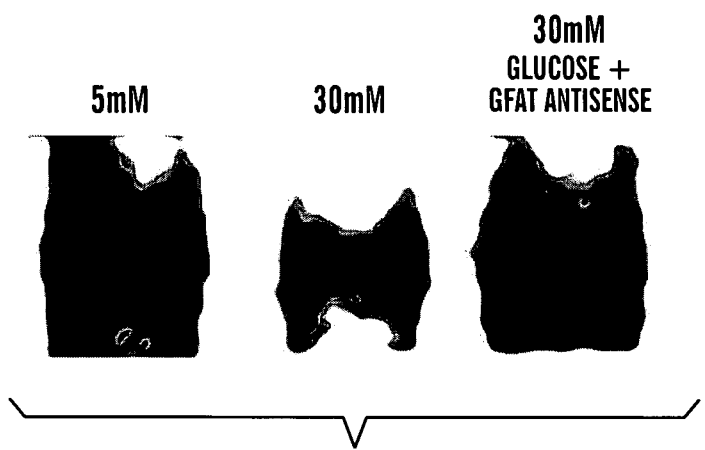
FIGS. 15A-B show high glucose (30 mM) impairs the association between p300 and PPARγ. This effect was abolished by inhibiting GFAT.
Figure 15B:
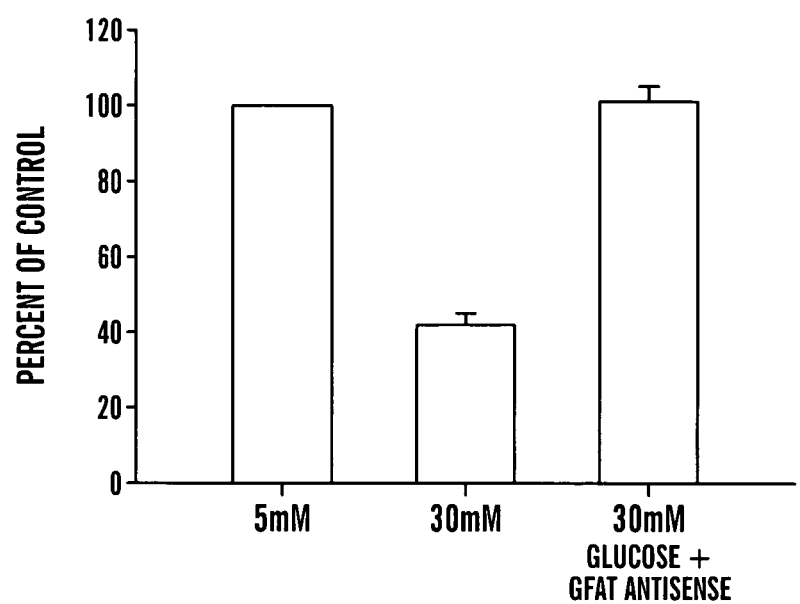

Since the HIF-1 transcriptional complex is comprised of several co-activators, it was also examined whether p300, the major co-activator of the HIF-1, was also glycosylated. While many transcription factors have been found to associate with p300 constitutively, some cases have been identified where this interaction is modulated by post-translational modification (Zanger et al., "CREB Binding Protein Recruitment to the Transcription Complex Requires Growth Factor-Dependent Phosphorylation of its GF Box," *Mol Cell* 7:551-8 (2001); Soutoglou et al., "Acetylation Regulates Transcription Factor Activity at Multiple Levels," *Mol Cell* 5:745-51 (2000), which are hereby incorporated by reference in their entirety). Repeating the HIF-1 experiments, it was also found that p300 also serves as a substrate for post-translational O-linked glycosylation in conditions of high glucose. This was physiologically significant since the association of p300 with the transcription factor peroxisome proliferator-activated receptor gamma (PPARγ) was reduced in conditions of high glucose compared to normal glucose by co-immunoprecipitation assays (FIG. 15). Interestingly, blockade of the rate-limiting enzyme of hexosamine biosynthesis, glutamine: fructose-6-phosphate amidotransferase (GFAT) with antisense oligonucleotides reduced the amount of O-linked glycosylation of p300 in high glucose nearly three-fold, and restored the p300/PPARγ interaction to levels comparable to cells grown in normal glucose (FIGS. 15A-B). This suggests that the recruitment of p300 to transcriptional complexes is impaired in conditions of high glucose, which can be reversed by preventing glucose-induced O-linked glycosylation. The physiologic relevance of O-linked glycosylation of HIF-1α is unclear. However, the demonstration that glycosylation modifies p300 function suggests a possible mechanism by which the HIF-1 transcriptional complex fails to upregulate VEGF expression, due to its inability to recruit and/or associate with co-activators required for transcriptional activation (i.e. p300).

Example 7

Hyperglycemia-Induced Reactive Oxygen Species Activate Pathways of Cellular Damage, Impairing Endothelial Cell Function The data presented thus far have examined the mechanisms responsible for initial observations that high glucose levels, both in vivo and in vitro, produce profound deficits in the ability to upregulate VEGF under hypoxic conditions.

Figure 16A:
FIGS. 16A-C show pathways of cellular damage resulting from reactive oxygen species can be selectively targeted and prevented.
Figure 16B:
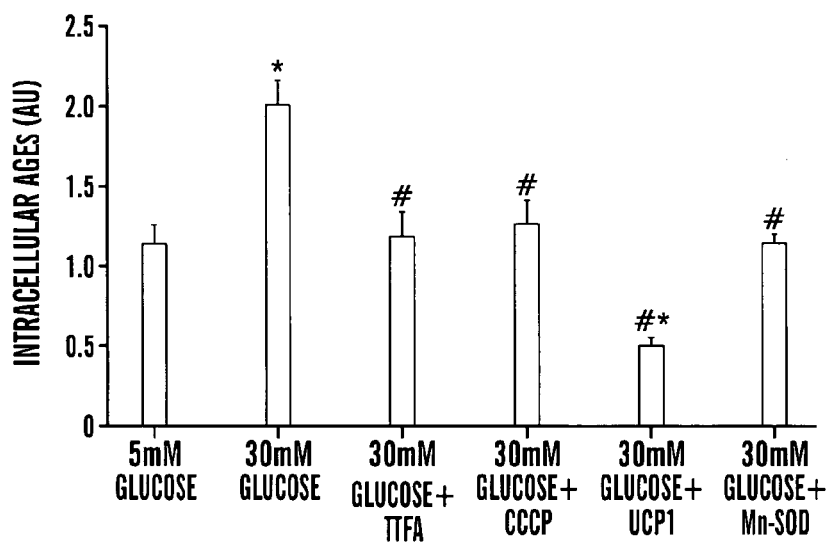
Figure 16C:

Although there is significant literature examining hyperglycemia-induced vascular damage in non-ischemic settings, very few studies have examined the effect of hyperglycemia-induced cellular damage on vascular functions in ischemic settings. This is of clinical importance, as most situations requiring new vascular growth occur in scenarios characterized by significant tissue hypoxia. It has been demonstrated that endothelial cells grown in high glucose in vitro show increased mitochondrial production of ROS. This results in increased hexosamine pathway activity with increased glycosylation of certain transcription factors (SP1) and signaling molecules (eNOS), increased PKC activity resulting in part in increased NFkB activity, greater accumulation of AGEs, and increased flux through the sorbitol pathway (FIG. 16). The downstream consequences of these intracellular events likely result in impaired neovascularization observed in vivo, but the intermediate steps remain unclear.

Example 8

Diabetic Cells are Impaired in Functions Critical for Angiogenesis

While it is clear that VEGF expression is altered in diabetic states, it has also been demonstrated that diabetic cells are impaired in other ways. Fibroblasts isolated from diabetic mice (db/db) show dramatic decreases in migration (four-fold less) than normal fibroblasts on collagen and fibronectin using a gold salt phagokinetic migration assay. When the haptotactic response of these cells was examined using a modified Boyden chamber migration assay, a similar decrease of 77% in migration in response to serum and PDGF was observed (Lerman et al., "Cellular Dysfunction in the Diabetic Fibroblast: Impairment in Migration, Vascular Endothelial Growth Factor Production, and Response to Hypoxia," *Am J Pathol* 162:303-12 (2003), which is hereby incorporated by reference in its entirety).

Figure 17A:
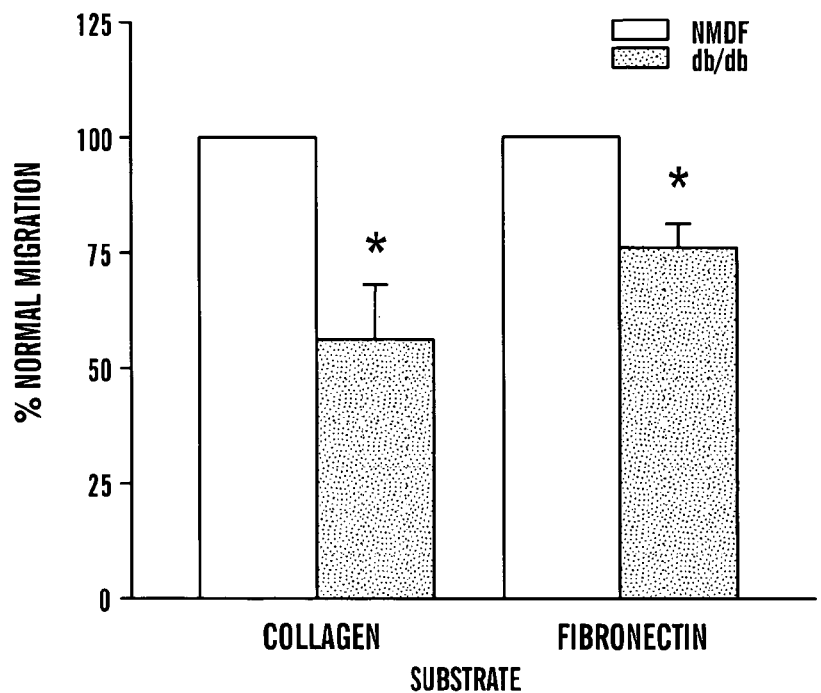
FIGS. 17A-B show fibroblasts from diabetic mice do not demonstrate a normal hypoxia-induced increase in migration seen in non-diabetic cells ($p<0.05$).
Figure 17B:
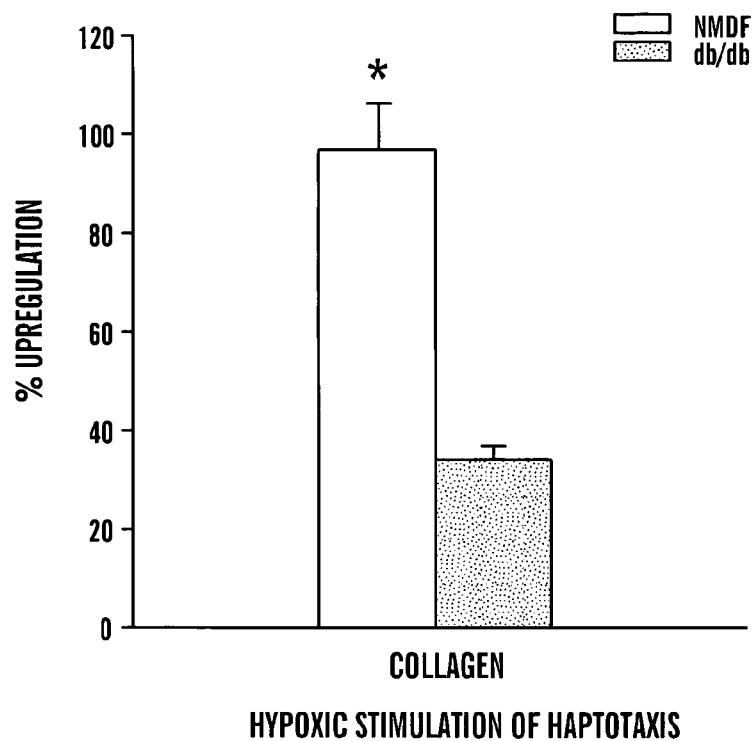

Once again, this difference was accentuated by hypoxia (FIG. 17). Whereas migration in normal cells was upregulated by hypoxia (two-fold), diabetic cells showed no difference in the rate of migration in hypoxia. These assays again emphasize the profound impact that diabetes has on cellular function, and that this impact is magnified under hypoxic conditions.

Figure 18A:
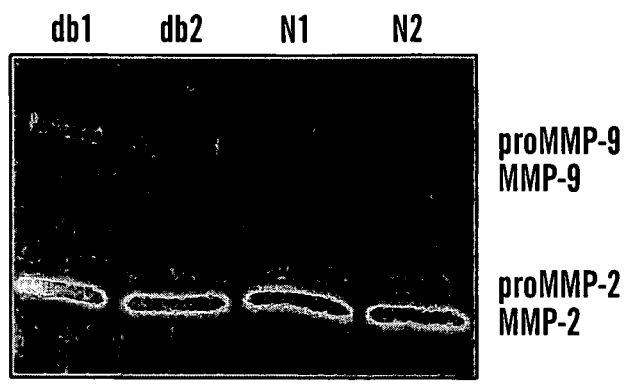
FIGS. 18A-B show fibroblasts from diabetic mice produce more pro-MMP-9, but not active MMP-9 ($p<0.001$).
Figure 18B:
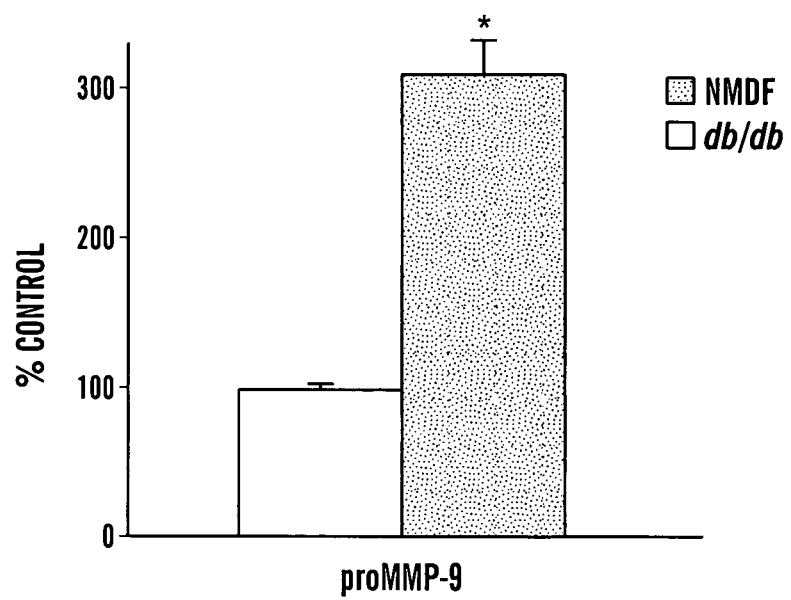

These migration differences may be due to differential expression of members of the matrix metalloproteinase (MMP) family in diabetic fibroblasts. It has been demonstrated that diabetic fibroblasts have greater levels of pro-MMP-9 than normal fibroblasts, but no differences in active MMP-9 or active/pro-MMP-2 (FIG. 18). This confirms similar findings in endothelial cells cultured in high glucose (Uemura et al., "Diabetes Mellitus Enhances Vascular Matrix Metalloproteinase Activity: Role of Oxidative Stress," *Circ Res* 88:1291-8 (2001), which is hereby incorporated by reference in its entirety). Furthermore, these findings suggest that diabetic cellular dysfunction is not characterized by a simple downregulation of all cellular proteins or functions, but involves selective modulation of specific genes and proteins.

Example 9

Figures 19A, 19B:
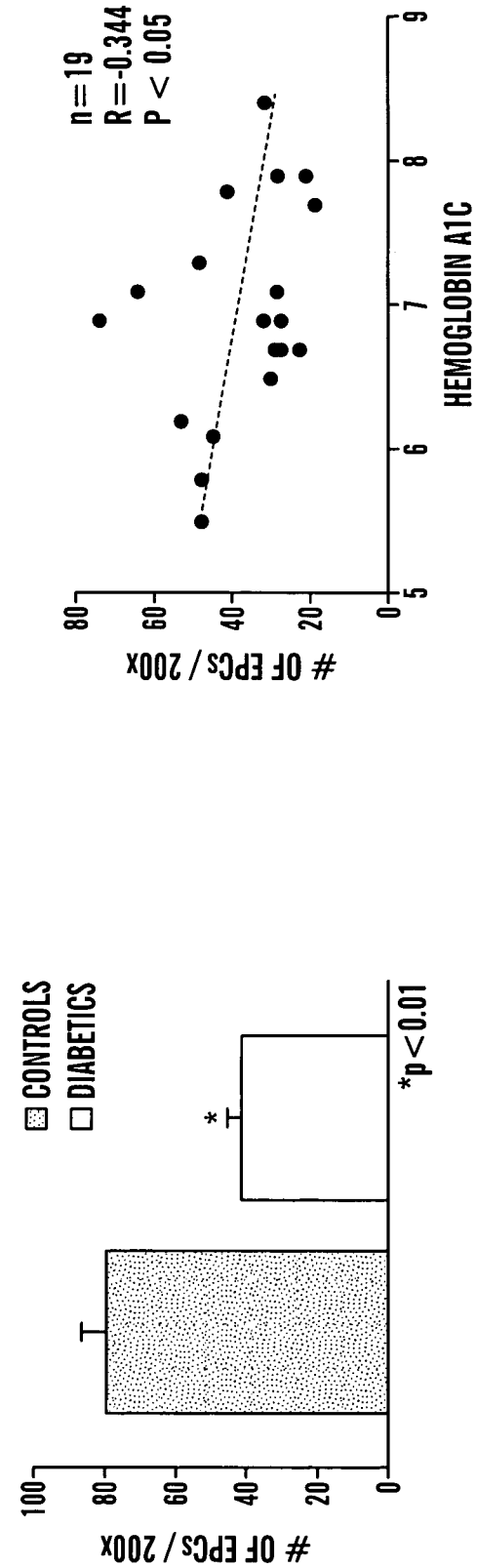
FIGS. 19A-D show EPCs from Type II diabetics proliferate less during expansion (A) which inversely correlated with HbA1c levels (B). Fewer EPC clusters formed in culture (C), which was also inversely correlated to the total number of years with diabetes.
Figure 19D:
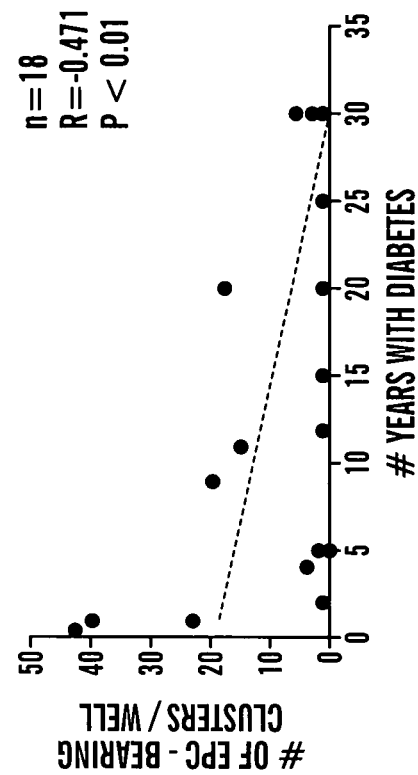
Figure 19C:
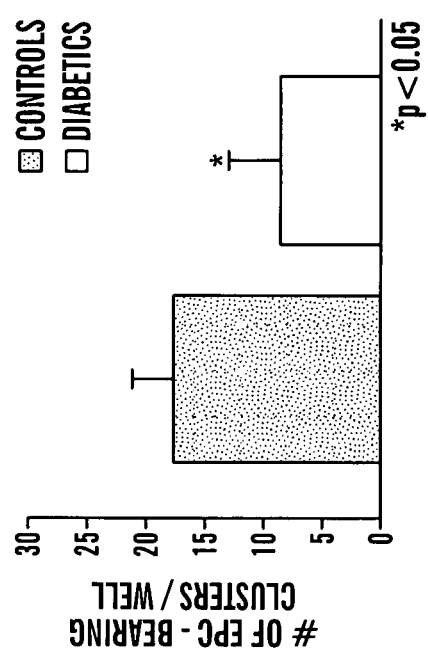
Figures 20A, 20B, 20C:
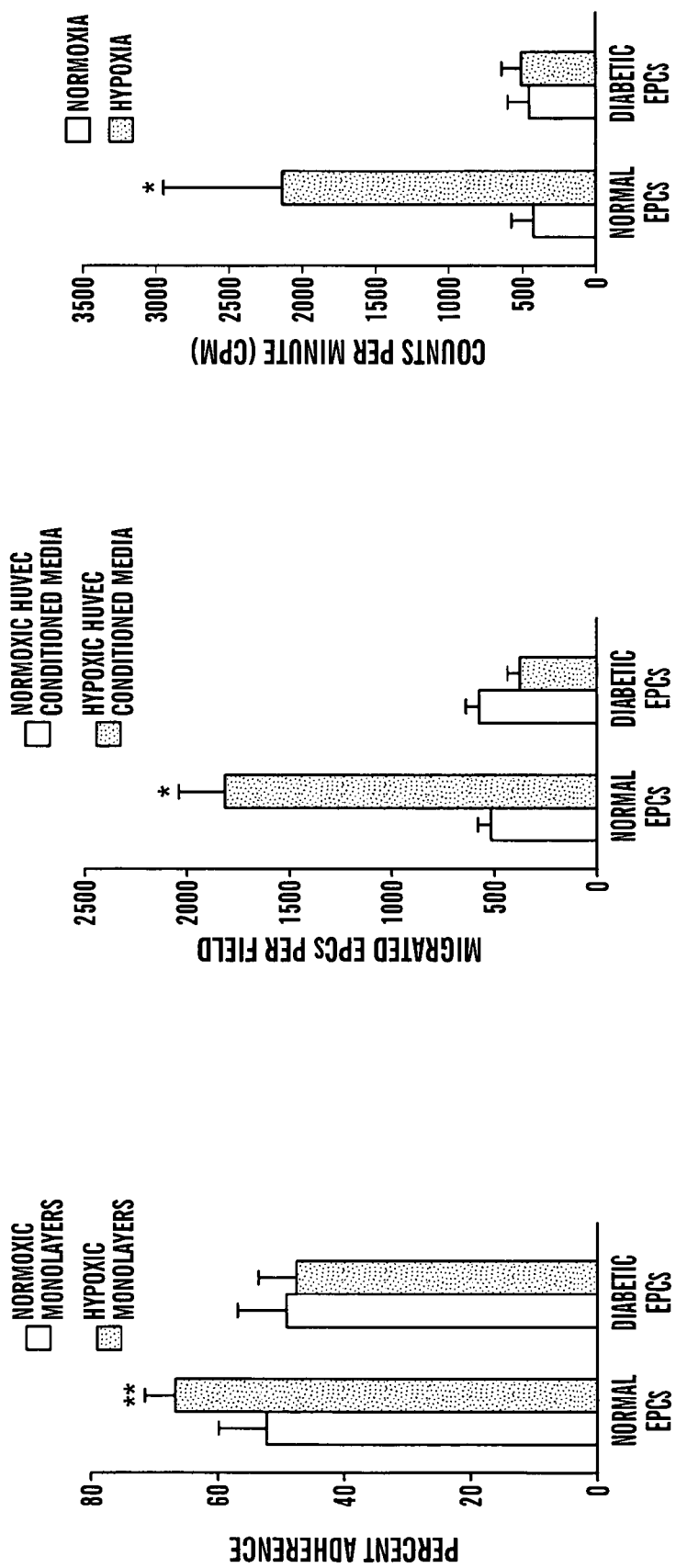
FIGS. 20A-C show EPCs from Type II diabetic patients are impaired in their ability to adhere, migrate, and proliferate in response to hypoxic stimuli ($\&=p<0.001$, $\&\&=p<0.05$).

Endothelial Progenitor Cells from Type II Diabetic Patients are Impaired in their Ability to Proliferate, Adhere, and Incorporate into Vascular Structures Hyperglycemic alterations in the effector cells of vasculogenesis, the endothelial progenitor cell or precursor cell remain poorly defined. Recently, it was demonstrated that endothelial progenitor cells (EPCs) harvested from Type II diabetic patients exhibit reduced proliferation, adhesion, and incorporation into vascular structures as compared to age matched controls under normoxic conditions (Tepper et al., "Human Endothelial Progenitor Cells From Type II Diabetics Exhibit Impaired Proliferation, Adhesion, and Incorporation Into Vascular Structures," *Circulation* 106:2781-6 (2002), which is hereby incorporated by reference in its entirety). Diabetic cultures contained significantly fewer EPCs after 7 days of expansion (FIG. 19), and this was inversely correlated with $HbA_{1c}$. Additionally, significantly fewer EPC-bearing clusters were noted in the cultures of diabetic patients. This was inversely correlated with the number of years of clinical diabetes (R=−0.471, P<0.01). Functionally, these cells were found to adhere less to TNF-α activated endothelial monolayers but exhibited normal adhesion to quiescent endothelial monolayers, which suggests that their ability to respond to environmental cues is deficient. This was confirmed with in vitro angiogenesis assays, which demonstrated that fewer diabetic EPCs were incorporated into tubules on Matrigel when compared to age-matched controls.

Example 10

Endothelial Progenitor Cells from Diabetic Patients have an Impaired Ability to Respond to Hypoxia Given preliminary data suggesting that diabetic cells have an impaired response to hypoxia, studies in EPCs have been to specifically examine the response of these cells to an ischemic environment. It was demonstrated that EPCs from Type II diabetic patients were impaired in their ability to adhere to hypoxic endothelial monolayers, migrate towards conditioned media from hypoxic endothelial cells, and proliferate a hypoxic environment (FIGS. 10A, B, C, respectively). This may be reflective of an impaired ability of these cells to sense and respond appropriately to hypoxic environmental cues, resulting in poor neovascularization.

Example 11

Deferoxamine Prevents Hyperglycemia-Induced Reactive Oxygen Production in Vascular Endothelial Cells Cultured vascular endothelial cells were treated with deferoxamine to determine the effect of deferoxamine on hyperglycemia-induced reactive oxygen production by those cells.

Cell culture conditions: For ROS measurement, bovine aortic endothelial cells (BAECs, passage 4-10) were plated in 96 well plates at 100,000 cells/well in Eagle's MEM containing 10% FBS, essential and nonessential amino acids, and antibiotics. Cells were incubated with either 5 mM glucose, 30 mM glucose, 30 mM glucose plus 100 micromolar deferoxamine, 30 mM glucose plus 250 micromolar deferoxamine. The deferoxamine was freshly prepared and added to the cells on three consecutive days. The ROS measurements were performed 72 hrs after the initial treatment.

Intracellular reactive oxygen species measurements: The intracellular formation of reactive oxygen species was detected using the fluorescent probe CM-H2DCFDA (Molecular Probes). Cells (1×105 ml-1) were loaded with 10 iM CM-H2DCFDDA, incubated for 45 min at 37° C., and analyzed in an HTS 7000 Bio Assay Fluorescent Plate Reader (Perkin Elmer) using the HTSoft program. ROS production was determined from an H2O2 standard curve (10-200 nmol ml-1).

Figure 21:
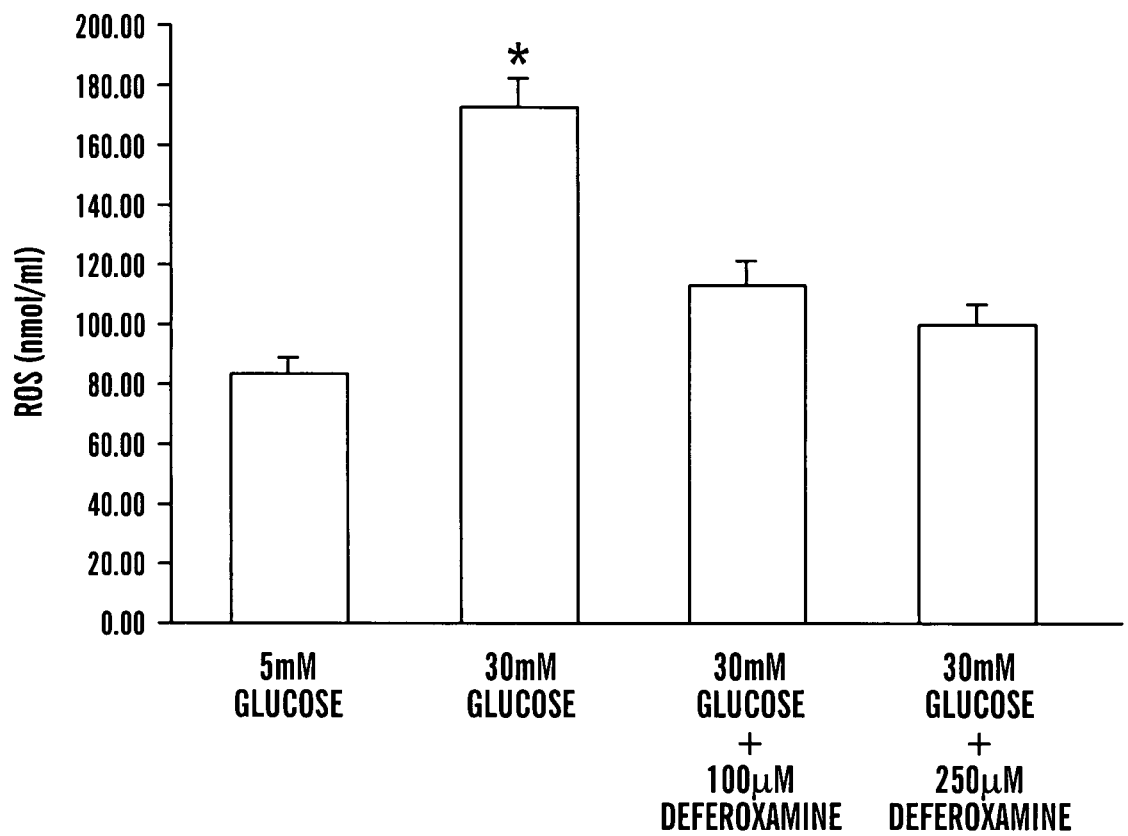
FIG. 21 shows the effect of deferoxamine on hyperglycemia-induced ROS.

As shown in FIG. 21 deferoxamine inhibited production of ROS in vascular endothelial cells in culture. Diabetic levels of hyperglycemia cause increased ROS (superoxide) production in these cells (FIG. 21, bar 2). Adding 250 µM deferoxamine completely prevents this damaging effect (FIG. 21, bar 4).

Thus, the iron chelator deferoxamine has a profound effect on vascular endothelial cells—i.e. it prevents completely hyperglycemia-induced overproduction of hydroxyl radicals (FIG. 21).

Example 12

Normalizing Excess Mitochondrial Superoxide Production Inhibits Hyperglycemia-Induced Increases in Intracellular Free Iron in Aortic Endothelial Cells For free intracellular iron measurement, bovine aortic endothelial cells ("BAECs", passage 4-10) were plated in 24 well plates at 500,000 cells/well in Eagle's MEM containing 10% FBS, essential and nonessential amino acids, and antibiotics. Cells were infected with UCP-1, Mn-SOD or empty adenoviral vectors, respectively, for 48 hours. 30 mM glucose was added to each well that was infected with the adenovirus. Uninfected cells were incubated with 5 mM and 30 mM glucose as controls. The free intracellular iron was detected after 24 hours.

In order to detect intracellular free iron, cells were loaded with fura-2 AM in the dark at 37° C. for 15 min in 1 ml of TBSS containing 5 µM fura-2 AM. After loading, cells were incubated with TBSS with 1 ml of 20 µM EDTA for 5 min. (Kress et al., "The Relationship between Intracellular Free Iron and Cell Injury in Cultured Neurons, Astrocytes, and Oligodendrocytes", *J. Neuro.*, 22(14):5848-5855 (2002), which is hereby incorporated by reference in its entirety). Fluorescence was detected using an Olympus IX70 with 10× planapo objectives, run by I.P. Lab Spectrum on a Power PC computer. Analysis was performed with I.P. Lab Spectrum.

Figure 22:
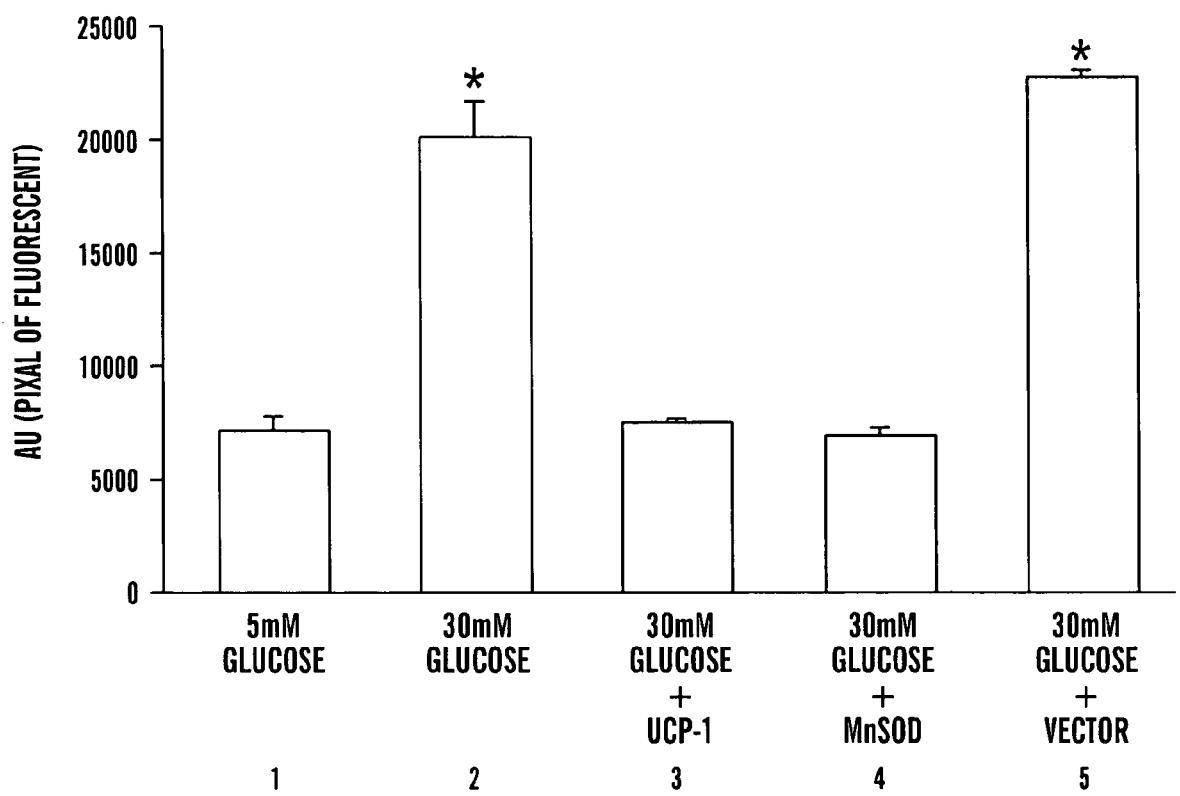
FIG. 22 shows the free intracellular iron measurement in bovine aortic endothelial cells after infection with UCP-1, Mn-SOD or empty adenoviral vectors and subsequent treatment with 5 mM or 30 mM glucose. The x-axis shows the different treatments. The y-axis shows fluorescence units indicating the amount of free iron.

As shown in FIG. 22, bar 2, hyperglycemia, increased the amount of free iron by nearly 3-fold. Since the probe fura-2 AM specifically detects $Fe^{3+}$ iron, this shows that it is free $Fe^{3+}$ iron which is increased. Inhibition of this effect by overexpression of uncoupling protein-1, a mitochondrial protein that prevents superoxide formation by the electron transport chain (bar 3) demonstrates that the mitochondria are the origin of the hyperglycemia-induced-superoxide. Inhibition of this effect by overepression of MnSOD, the mitochondrial isoform of the enzyme superoxide dismutase (bar 4), demonstrates that mitochondrial superoxide is the reactive oxygen species that induces increased intracellular free iron.

Example 13

Deferoxamine Inhibits Hyperglycemia-Induced Increases in Intracellular Free Iron in Aortic Endothelial Cells Bovine aortic endothelial cells ("BAECs", passage 4-10) were plated in 24 well plates at 500,000 cells/well in Eagle's MEM containing 10% FBS, essential and nonessential amino acids, and antibiotics. Cells were incubated with either 5 mM glucose, 30 mM glucose, or 30 mM glucose plus 100 µM deferoxamine. Free intracellular iron measurement was performed 24 hours later. To detect intracellular free iron, cells were loaded with fura-2 AM as described above in Example 12.

As shown in FIG. 23B, hyperglycemia (accomplished by 30 mM glucose incubation) dramatically increases intracellular free iron in the $Fe^{3+}$ form compared to normal glycemia, as shown in FIG. 23A (accomplished by 5 mM glucose treatment), as it did in Example 12. As shown in FIG. 23C, the $Fe^{3+}$-specific iron chelator deferoxamine (100 µM) completely prevents this effect of hyperglycemia.

Example 14

Deferoxamine and the Hydroxyl Radical Scavenger DMSO Both Inhibit Hyperglycemia-Induced Increases in DNA Strand Breakage in Aortic Endothelial Cells Bovine aortic endothelial cells ("BAECs", passage 4-10) were plated in 10 mm cell culture plates until confluent. Cells were incubated with either 5 mM glucose, 30 mM glucose, 30 mM glucose plus 100 uM deferoxamine (DFO), or 30 mM glucose plus 100 µM DMSO, a hydroxyl radical scavenger, for 7 days. Medium with reagents was changed daily. DNA strand breakage was detected using the Comet assay method.

DNA breakage detection was performed using the Comet Assay kit (Trevigen Gaitherburg Md.). Briefly, single cell electrophoresis was performed on the cometslide for 10 min at 1 volt/cm (measured from one electrode to another). After air-drying, the cometslide was stained with SYBR green. Fluorescence was detected using the Olympus IX70 fluorescent microscope and analysis of the fluorescent density of DNA breakage (length of tail) was performed using Image J software.

Figure 24A:
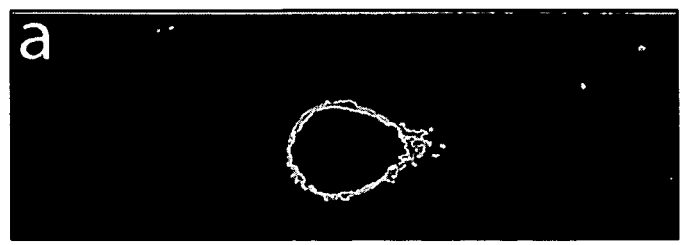
FIGS. 24A-D show, respectively, DNA strand breakage in aortic endothelial cells after incubation with 5 mM or 30 mM glucose or 30 mM glucose plus 100 μM deferoximamine for 7 days.
Figure 24B:
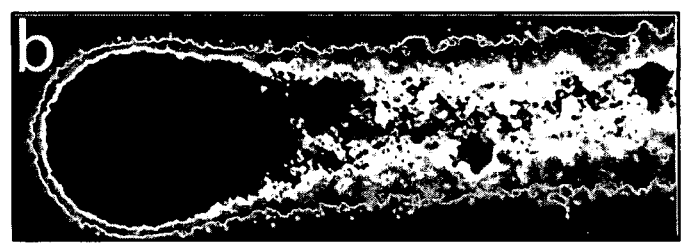
Figure 24C:
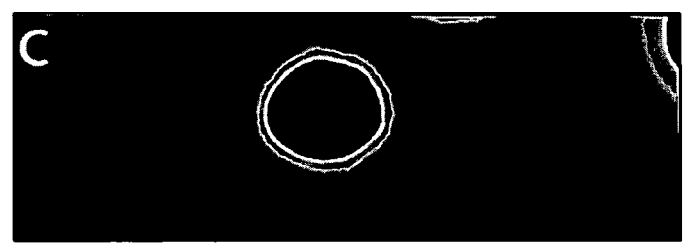
Figure 24D:
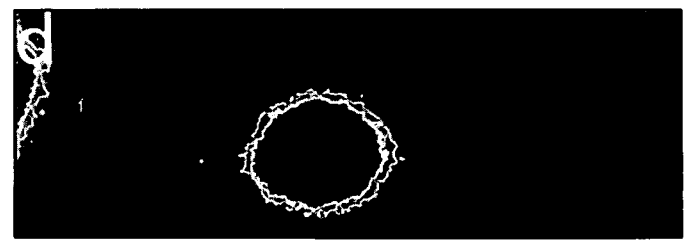

It has previously been shown that hyperglycemia-induced superoxide production by the mitochondrial electron transport chain causes DNA strand breakage in aortic endothelial cells, as demonstrated in FIG. 24B. The data shown in FIG. 24C prove that this effect requires the superoxide-induced increase in free $Fe^{3+}$. Similarly, the data shown in FIG. 24D show that this effect requires superoxide-induced hydroxyl radical production. Together, these data show that deferoxamine treatment prevents hydroxyl radical generation and subsequent DNA strand breakage, despite the continued overproduction of superoxide by the mitochondrial electron transport chain.

Example 15

Deferoxamine and the Hydroxyl Radical Scavenger DMSO Both Inhibit Hyperglycemia-Induced Increases in PARP Activity in Aortic Endothelial Cells Bovine aortic endothelial cells ("BAECs", passage 4-10) were plated in 10 mm cell culture plates until confluent. Cells were incubated with either 5 mM glucose, 30 mM glucose, 30 mM glucose plus 100 µM deferoxamine, or 30 mM glucose plus 100 µM DMSO for 6 days and medium changed daily.

The 3H-NAD incorporation method was used to assess PARP activity. BAECs were incubated with buffer which was composed of 56 mM Hepes (pH 7.5), 28 mM KCl, 28 mM NaCl, 2 mM MgCl$_2$, 0.01% digitonin, 25 mM NAD$^+$, and 1 µCi/ml $^3$HNAD$^+$ for 10 min at 37° C. TCA was added to precipitate ribosylated protein and cells were lysed in 2% NaOH. Detection of incorporated $^3$H-NAD was performed using a scintillation counter, and PARP activity determined according to the number of $^3$H-NAD dpm.

Figure 25:
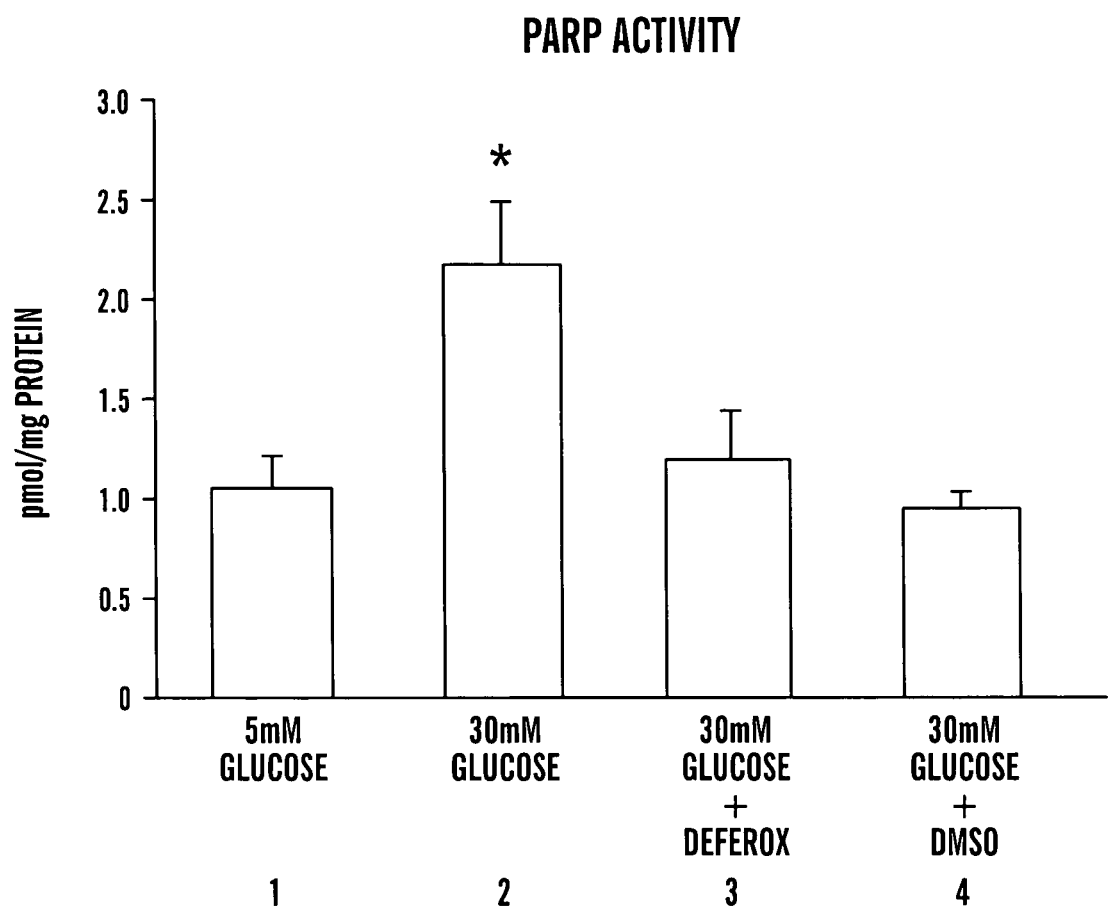
FIG. 25 shows PARP activity in aortic endothelial cells after incubation with 5 mM or 30 mM glucose, 30 mM glucose plus 100 μM deferoxamine, or 30 mM glucose plus 100 μM DMSO for 6 days. $^3$H-NAD incorporation was used to assess PARP activity. The x-axis shows the different treatments. The y-axis shows the PARP activity as measured in pmol/mg protein.

It has previously been shown that hyperglycemia-induced superoxide production by the mitochondrial electron transport chain causes DNA strand breakage which then activates the enzyme poly (ADP-ribose)polymerase (PARP) in aortic endothelial cells, as shown in FIG. 25. The data shown in bar 3 prove that this effect requires the superoxide-induced increase in free Fe$^{3+}$. Similarly, the data shown in bar 4 show that this effect requires superoxide-induced hydroxyl radical production. Together, these data show that deferoxamine treatment prevents hydroxyl radical generation, subsequent DNA strand breakage, and resultant PARP activation, despite the continued overproduction of superoxide by the mitochondrial electron transport chain.

Example 16

Deferoxamine Prevents Hyperglycemia-Induced Inhibition of Prostacyclin Synthase (PGF-1α) in Aortic Endothelial Cells Bovine aortic endothelial cells ("BAECs", passage 4-10) were plated in a 24-well plate (50,000 cell/well). Cells were incubated with either 5 mM glucose, 30 mM glucose, or 30 mM glucose plus 100 µM deferoxamine. The prostacyclin synthase product, PGF-1α, was measured 24 hours later.

Prostacyclin synthase activity measured as the concentration of the stable product of prostacyclin synthase, PGF-1α. A competitive immunoassay method (Correlate-EIA) was used for the quantitative determination of 6-keto-PGF1α. Samples (100 µl) collected from BAECs culture medium were added to the assay plate, which was precoated with antibody (6-keto-PGF1α, EIA conjugate solution). PGF1α concentration was calculated according to a standard curve, and data analysis performed using AssayZap software.

Figure 26:
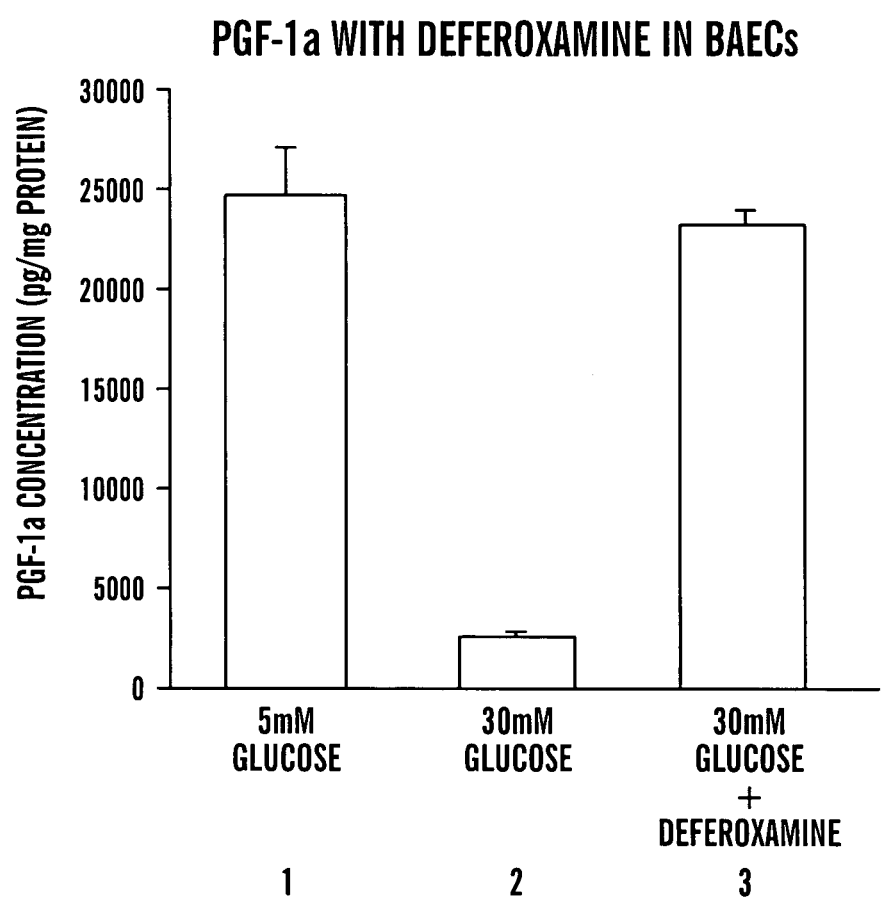
FIG. 26 shows prostacyclin synthase activity in aortic endothelial cells after 24 hour incubation with 5 mM or 30 mM glucose, or 30 mM glucose plus 100 μM deferoxamine. The x-axis shows the different treatments. The y-axis shows the prostacyclin synthase activity expressed as concentration of the prostacyclin synthase product PGF-1α.

It has previously been shown that hyperglycemia-induced superoxide production by the mitochondrial electron transport chain completely inactivates the endothelial enzyme prostacyclin synthase, which is a major natural defense against the development of atherosclerosis. In bar 2 of FIG. 26, hyperglycemia is shown to decrease the activity of this enzyme by over 90%. In contrast, bar 3 shows that hyperglycemia does not inhibit the activity of this important antiatherogenic enzyme at all when the superoxide-induced increase in free Fe$^{3+}$ is prevented by deferoxamine.

Example 17

Deferoxamine Prevents Diabetes-Induced Inhibition of Prostacyclin Synthase (PGF-1α) in Aortas of Diabetic Mice Male C57B16 mice (6-8 weeks old) were made diabetic by daily injections of 50 mg/kg streptozotocin in 0.05 M NaCitrate pH 4.5 after an eight hour fast, for five consecutive days. Two weeks after the initial injection the blood glucose was determined and the diabetic mice were randomized into two groups with equal mean blood glucose levels. Deferoxamine (10 mg/kg) was injected subcutaneously once per day for 7 days in one group of diabetic animals. The aortas were collected for prostacyclin synthase activity measurement Prostacyclin synthase activity measurement A competitive immunoassay method (Correlate-EIA) was used for the quantitative determination of 6-keto-PGF$_{1α}$. Mouse aortas were washed with PBS and incubated at 37° C. for 3 hours in 400 µl incubation buffer containing 20 mM TRIS buffer (pH 7.5), and 15 µM arachidonic acid. 100 µl of sample was used to measure the PGF1α.

Figure 27:
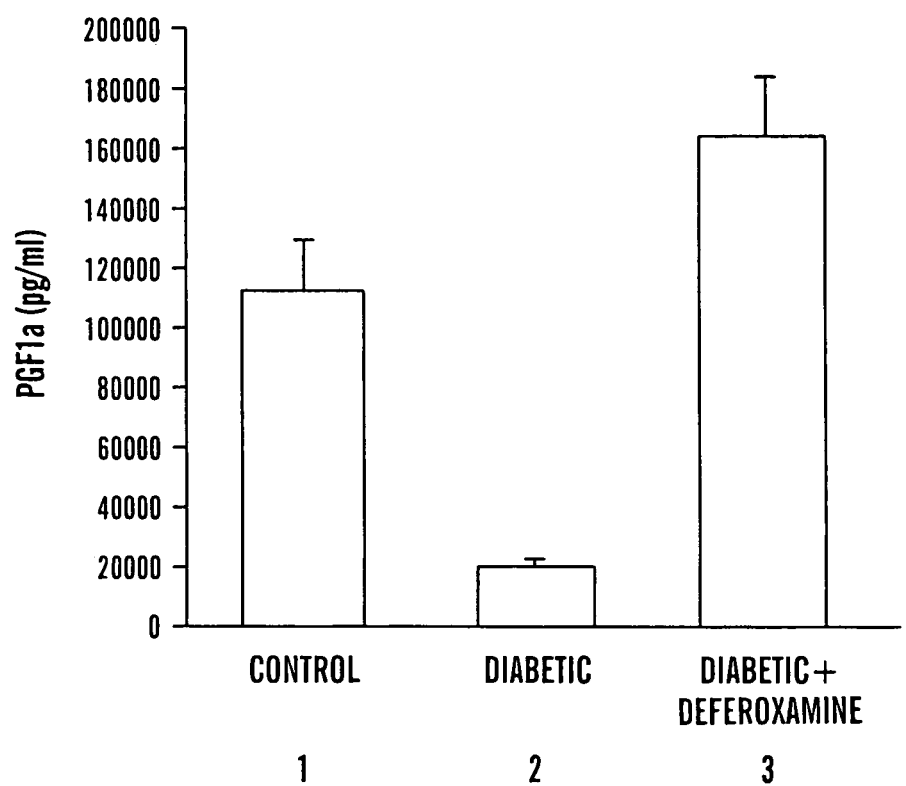
FIG. 27 shows prostacyclin synthase activity in aortas of diabetic and control mice after daily deferoxamine injections for 7 days. The x-axis shows the different treatments. The y-axis shows the prostacyclin synthase activity as measured by the concentration of the prostacyclin synthase product PGF-1α.

It has previously been shown that diabetes-induced superoxide production by the mitochondrial electron transport chain completely inactivates the endothelial enzyme prostacyclin synthase in aortas of diabetic mice. In bar 2 of FIG. 27, hyperglycemia is shown to decrease the activity of this enzyme in vivo by over 90%. In contrast, bar 3 of FIG. 27 shows that hyperglycemia does not inhibit the activity of this important antiatherogenic enzyme at all when the superoxide-induced increase in free Fe$^{3+}$ is prevented by deferoxamine.

Example 18

Deferoxamine Prevents Hyperglycemia-Induced Inhibition of Endothelial Nitric Oxide Synthase (eNOS) in Aortic Endothelial Cells Bovine aortic endothelial cells ("BAECs", passage 4-10) were plated in 24-well plate (50,000 cell/well). Cells were incubated with either 5 mM glucose, 30 mM glucose alone, or 30 mM glucose plus 1000 uM deferoxamine, for 24 hour. Six hours before eNOS activity determination, media without arginine was added to the cells to deplete endogenous arginine.

Measurement of eNOS activity was accomplished as follows. BAECs were incubated with 400 µl of PBS-$^3$H-arginine (1.5 µci/ml) buffer for 30 min at 37° C. The reaction was stopped by adding 1N TCA (500 µl/well, ice cold), the cells were freeze fractured in liquid nitrogen for 2 min and thawed at 37° C. for 5 min to obtain the cell lysate. After extraction with ether, the cell lysate was adjusted to pH 5.5 using Hepes buffer containing 2 mM EDTA and 2 mM of EGTA, then loaded onto Tris-formed DOWEX 50WX8 ion-exchange columns and $^3$H-citrulline collected. Detection of $^3$H-citrulline was performed using a liquid scintillation counter, and eNOS activity was calculated from the amount of $^3$H-citrulline generated.

Figure 28:
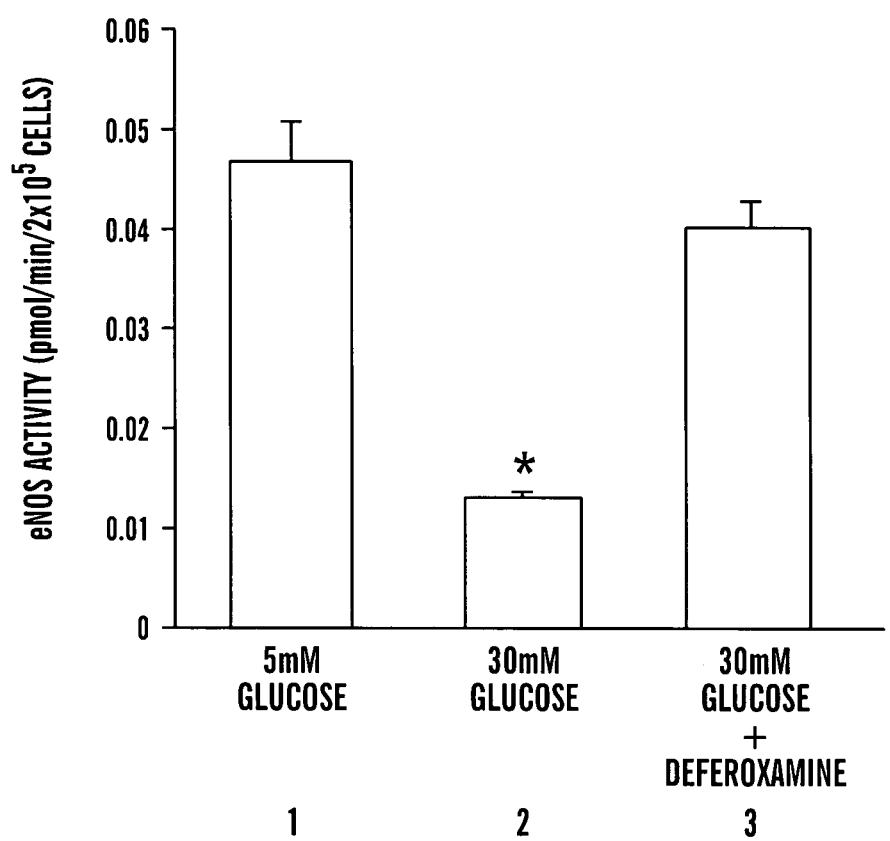
FIG. 28 shows eNOS activity in aortic endothelial cells after incubation with 5 mM or 30 mM glucose or 30 mM glucose plus 100 μM deferoxamine for 24 hours. The x-axis shows the different treatments. The y-axis shows the eNOS activity as a function of $^3$H-citrulline generated per minute per $10^5$ cells.

It has previously been shown that hyperglycemia-induced superoxide formation significantly inactivates another critical endothelial enzyme, endothelial nitric oxide synthase (eNOS). This enzyme plays a critical role in acute dilation of blood vessels in response to hypoxia, and a chronic role as another major defense against development and progression of atherosclerosis. In bar 2 of FIG. 28, hyperglycemia is shown to decrease eNOS activity by 65%. In contrast, bar 3 shows that hyperglycemia does not inhibit the activity of this important antiatherogenic enzyme at all when the superoxide-induced increase in free $Fe^{3+}$ is prevented by deferoxamine.

Example 19

Deferoxamine Prevents Diabetes-Induced Inhibition of Endothelial Nitric Oxide Synthase (eNOS) in Aortas of Diabetic Mice Male C57B16 mice (6-8 weeks old) were made diabetic by daily injections of 50 mg/kg streptozotocin in 0.05 M NaCitrate pH 4.5 after an eight hour fast, for five consecutive days. Two weeks after the initial injection, the blood glucose was determined and the diabetic mice were randomized into two groups with equal mean blood glucose levels. Deferoxamine (10 mg/kg) was injected subcutaneously once per day for 7 days in one group of diabetic animals. The aortas were collected for endothelial nitric oxide synthase (eNOS) activity measurement.

Measurement eNOS activity was accomplished as follows. Aortas were collected in liquid-nitrogen and tissue proteins isolated. Immunoprecipitation methods were used to purify the eNOS from tissue lysates. The purified eNOS immunocomplex was incubated with 100 µl of reaction buffer (3 µM Tetrahydrobiopterin, 1 mM NAPDH, 2.5 mM $CaCl_2$, 200 U Calmodulin, $^3$H-L-arginine 0.2 µCi) for 45 min at 37° C. with rolling. After the incubation, samples were loaded onto Tris-formed DOWEX 50WX8 ion-exchange column and $^3$H-citrulline was collected. $^3$H-citrulline was quantitated using a liquid scintillation counter and eNOS activity was calculated from the amount of $^3$H-citrulline generated.

Figure 29:
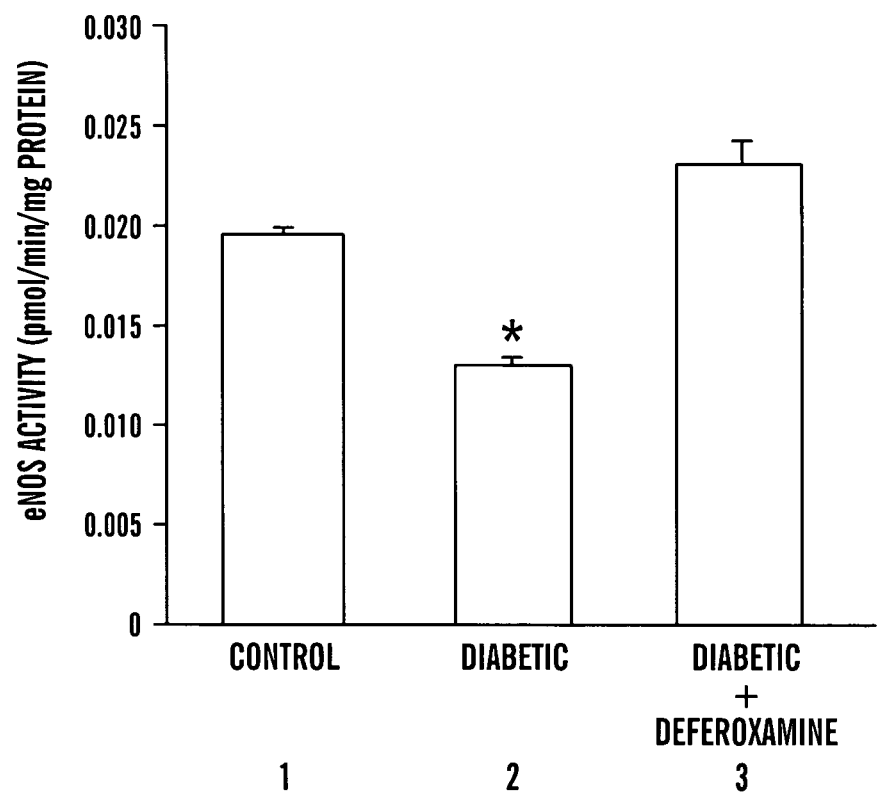
FIG. 29 shows eNOS activity in aortas of diabetic and control mice after daily deferoxamine injections for 7 days. The x-axis shows the different treatments. The y-axis shows the eNOS activity as a function of $^3$H-citrulline generated per minute per mg of protein.

It has previously been shown that diabetes-induced-induced superoxide production by the mitochondrial electron transport chain inactivates the endothelial enzyme eNOS in aortas of diabetic mice. In bar 2 of FIG. 29, diabetic hyperglycemia is shown to decrease the activity of this enzyme in vivo by 65%. In contrast, bar 3 shows that hyperglycemia does not inhibit the activity of this important antiatherogenic enzyme at all when the superoxide-induced increase in free $Fe^{3+}$ is prevented by deferoxamine.

Example 20

Diabetes-Induced Defect in Angiogenic Response to Ischemia

Figure 30A:
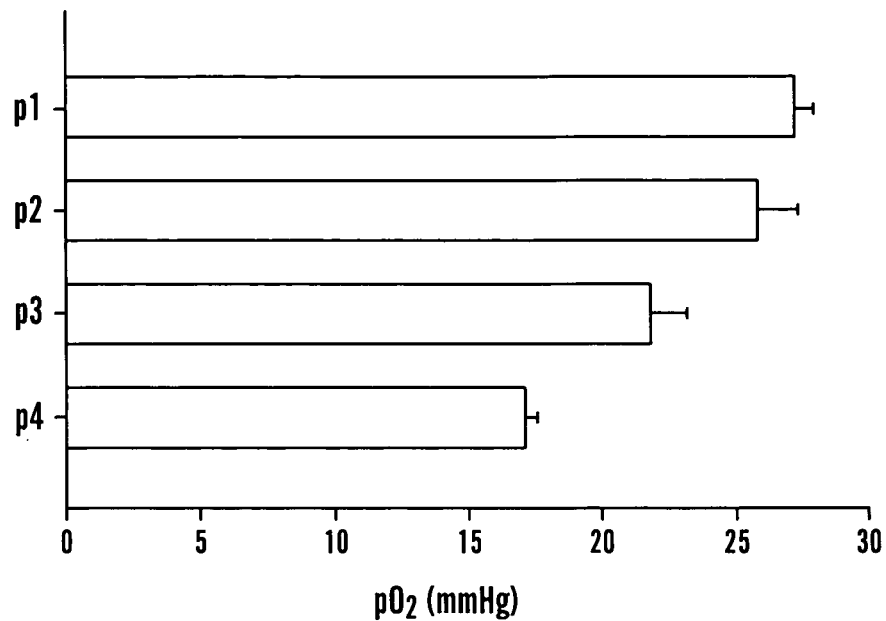
FIGS. 30A-F show a diabetes-induced defect in mouse angiogenic response to ischemia.
Figure 30B:
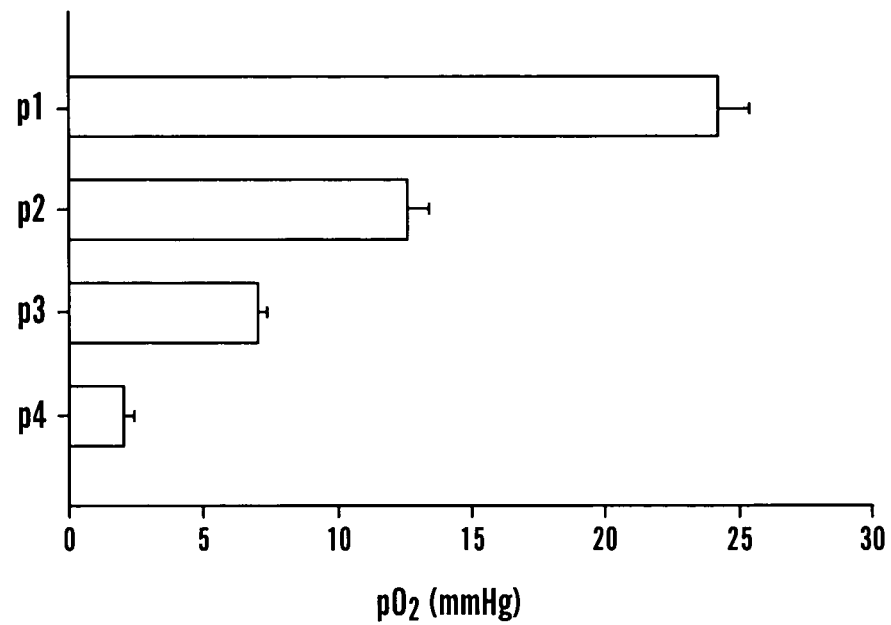
Figure 30C:
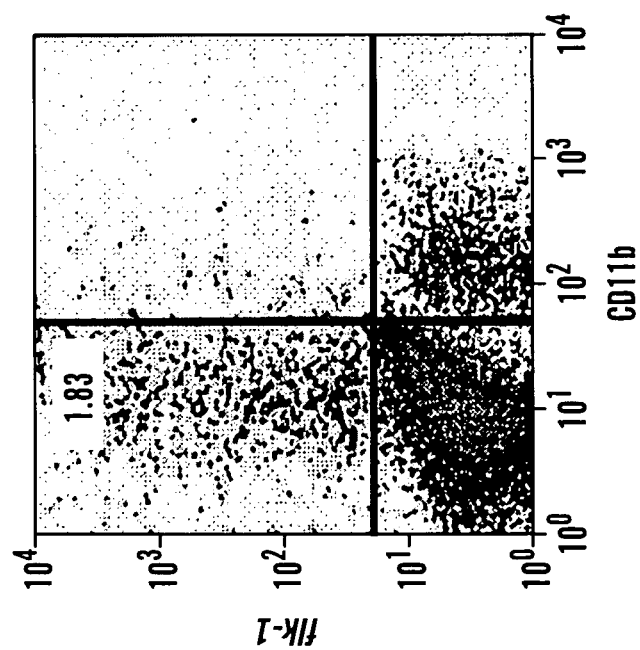
Figure 30D:
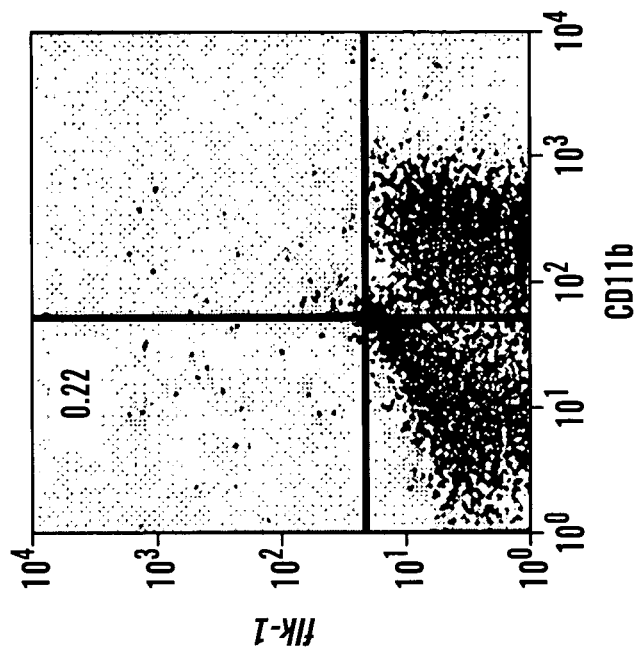
Figure 30E:
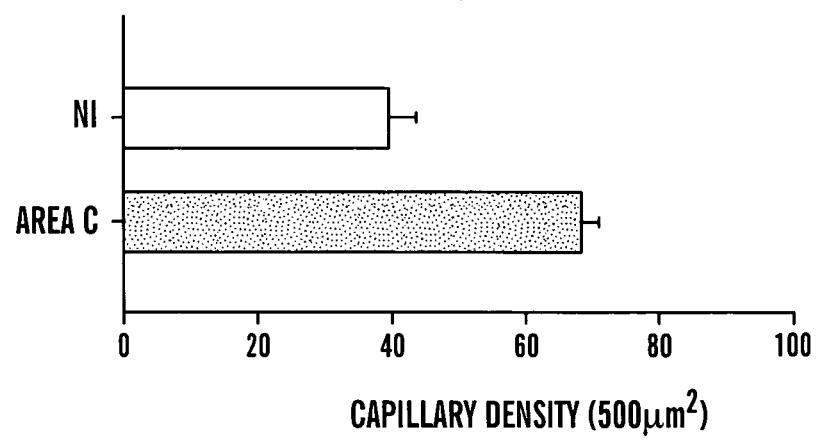
Figure 30F:
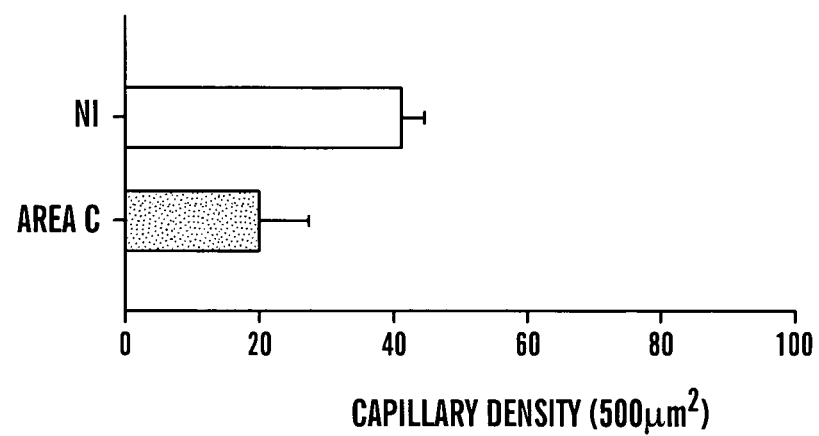

FIGS. 30A-B show that diabetic animals do not increase oxygenation by forming new vessels the way non-diabetic animals do. FIGS. 30C-D show that diabetic animals only mobilize 0.22 vs. 1.83% of bone marrow-derived endothelial precursor cells in response to ischemia. FIGS. 30E-F show (black bar) that diabetics do not increase capillary formation in ischemic tissue.

Researchers have created a novel model of graded ischemia in the dorsal soft tissue of mice. Since the vascular anatomy of the mouse dorsum is precisely known, and the major axial vessels can be easily visualized, this model creates a reliable zone of ischemia with a reproducible oxygen gradient in the tissue. This has been confirmed with direct tissue oxygen tension measurements utilizing four reference points (p1-p4) spaced 0.5 cm apart, proceeding from the least to most ischemic regions.

The mechanisms underlying this diabetes-induced defect are complex and incompletely understood, but appear to involve mitochondrial superoxide overproduction, since the defect is significantly prevented in diabetic transgenic mice which overexpress the mitochondrial isoform of SOD.

Example 21

Deferoxamine Treatment Corrects the Diabetes-Induced Defect in Angiogenic Response to Ischemia The effect of deferoxamine, an iron chelator, on ischemic neovascularization in streptozotocin-induced diabetic (STZ) and wild type C57 (WT) mice was examined. Male C57B16 mice (6-8 weeks old) were made diabetic by daily injections of 50 mg/kg streptozotocin in 0.05 M NaCitrate pH 4.5 after an eight hour fast, for five consecutive days. Two weeks after the initial injection the blood glucose was determined, the diabetic mice were randomized into two groups with equal mean blood glucose levels.

The treatment group was pretreated 7 days prior to having an ischemic flap created on their dorsum and throughout the experiment with daily injections of deferoxamine (10 mg/kg) subcutaneously once per day for 7 days in one group of diabetic animals.

Figure 31A:
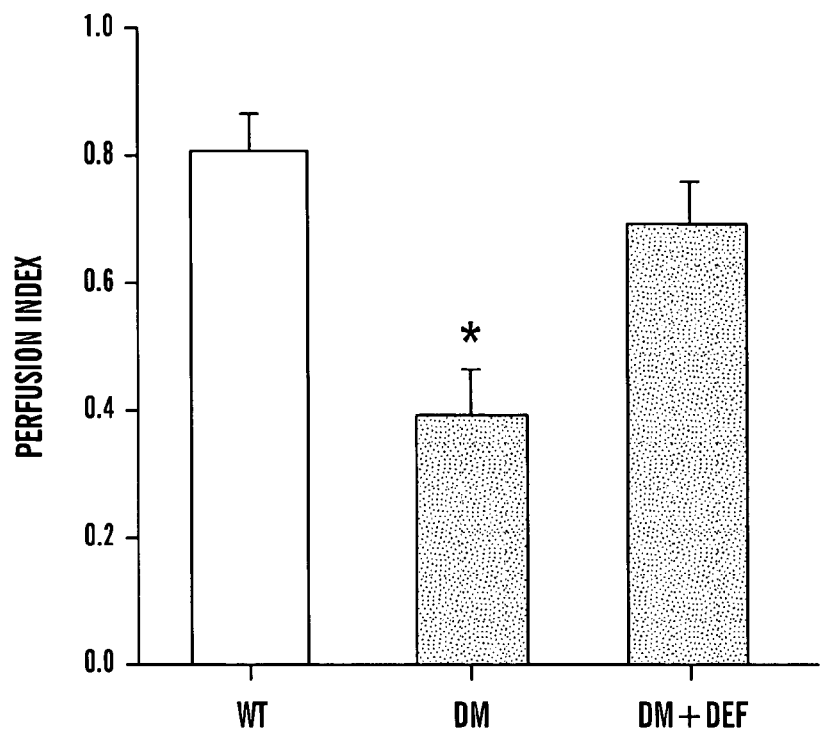
FIGS. 31A-C show that deferoxamine treatment corrects the diabetes-induced defect in mouse anigiogenic response to ischemia. The treatment groups were wild-type mice (WT), streptozotocin-induced diabetic mice (shown as STZ in FIG. 31C, and DM in FIGS. 31A-B), and deferoxamine-treated streptozotocin-induced diabetic mice (shown as STZ+deferox in FIG. 31C, and DM+DEF in FIGS. 31A-B).
Figure 31B:
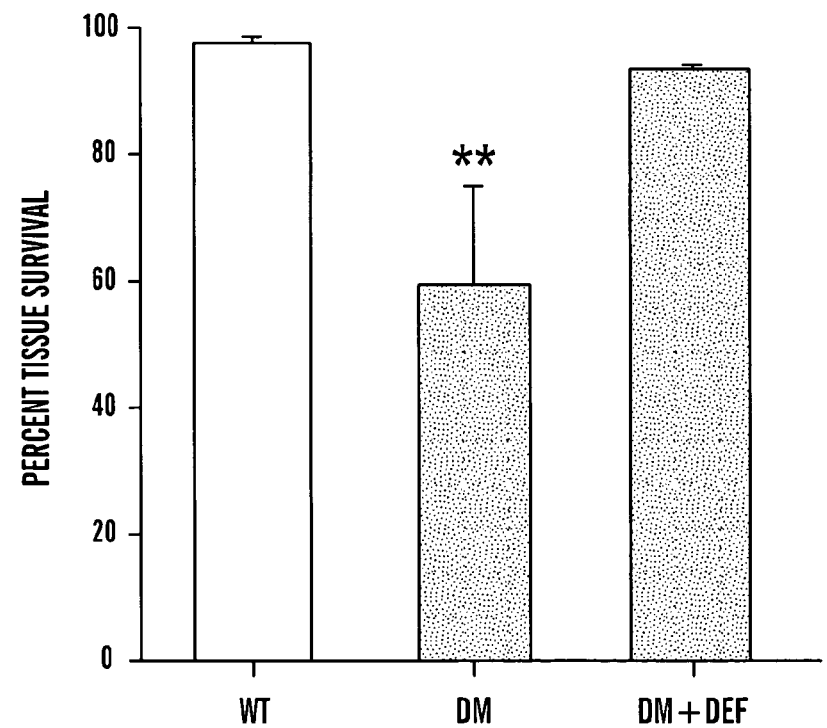
Figure 31C:
Figure 32:
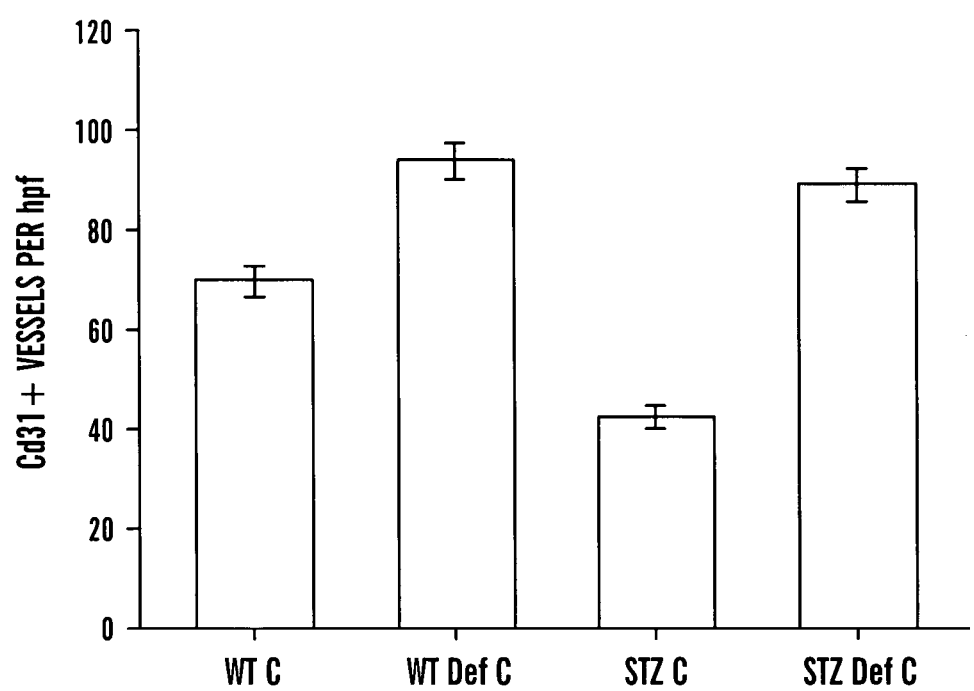
FIG. 32 shows CD 31 positive blood vessel counts in wild-type mice (WT C), wild-type mice treated with deferoxamine (WT Def C), streptozotocin-induced diabetic mice (STZ C), and streptozotocin-induced diabetic mice treated with deferoxamine (STZ Def C). The y-axis shows the CD 31 positive blood vessel counts per hpf (high powered field).
Figure 36:
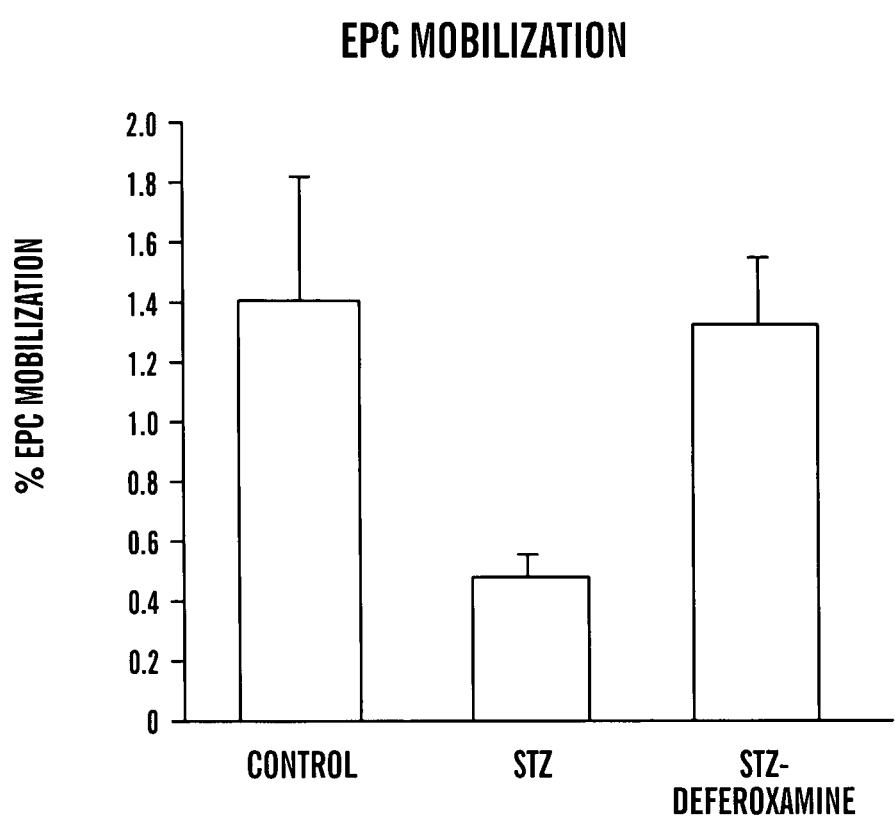
FIG. 36 is a bar chart showing EPC mobilization for control, STZ, and STZ-deferoxamine mice. EPC mobilization was determined at day 7 post-ischemic insult. Diabetes resulted in a 3-fold decrease in EPC mobilization. Deferoxamine restores ischemia specific EPC mobilization as compared to untreated STZ mice ($p<0.05$).

On day 7, it was found that blood flow was restored to normal in the STZ-deferoxamine group (DM+DEF) when compared with the non-diabetic untreated group (WT), and the severely impaired STZ-untreated group (DM), as assessed by Doppler and as shown in FIG. 31A. FIG. 31B shows tissue survival was restored to normal in the STZ-deferoxamine group (DM+DEF) when compared with the non-diabetic untreated group (WT), and the severely impaired STZ-untreated group (DM). CD31 positive blood vessel counts demonstrate that post-ischemic neovascularization was restored in the STZ-deferoxamine group (STZ Def C), as shown in FIG. 32. Interestingly, deferoxamine in the wild type mice (WT Def C) also improved neovascularization. EPC mobilization was also improved in the STZ-deferoxamine group when compared with the untreated STZ mice. Migration of diabetic bone marrow derived, lineage depleted cell population migration toward SDF was restored to normal when STZ mice were treated with deferoxamine. See FIG. 36.

These results show that treatment of diabetic animals with deferoxamine completely prevents the diabetes-induced defect in the normal angiogenic response to ischemia.

Example 22

MnTBAP Normalizes Diabetic Wound Healing

Figure 33B:
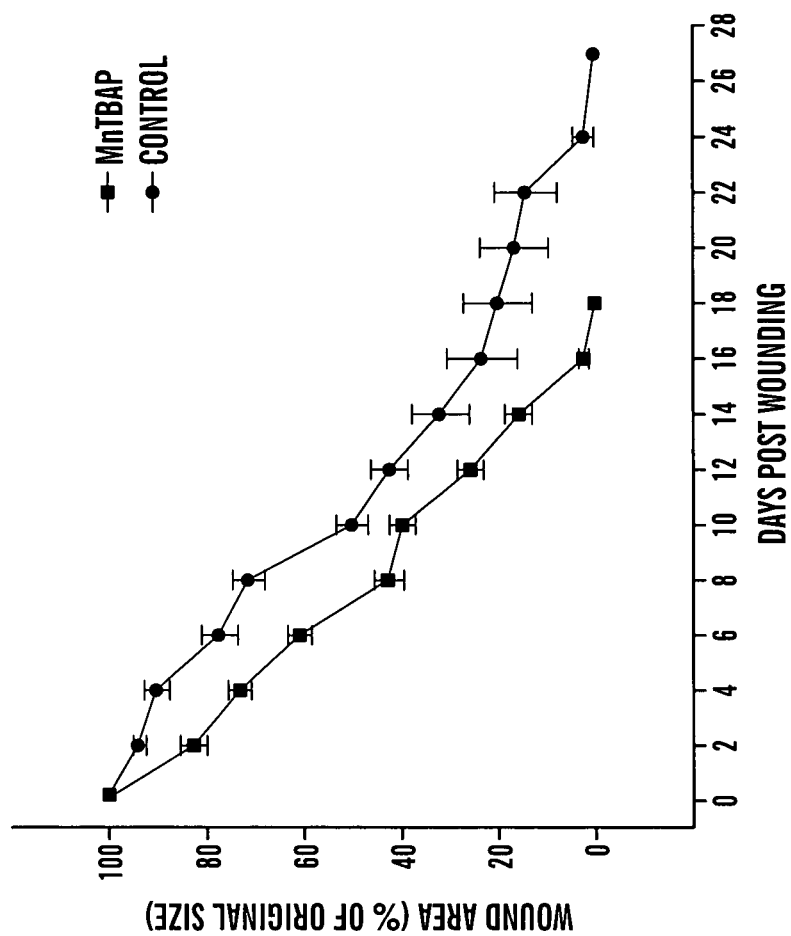
FIGS. 33A-B show wound closure in diabetic mice (control) and diabetic mice treated with MnTBAP (TBAP in FIG. 33A, MnTBAP in FIG. 33B). The y-axis of FIG. 33B shows the wound area as a measure of the % of the original wound size. The x-axis shows the days after wounding.
Figure 33A:
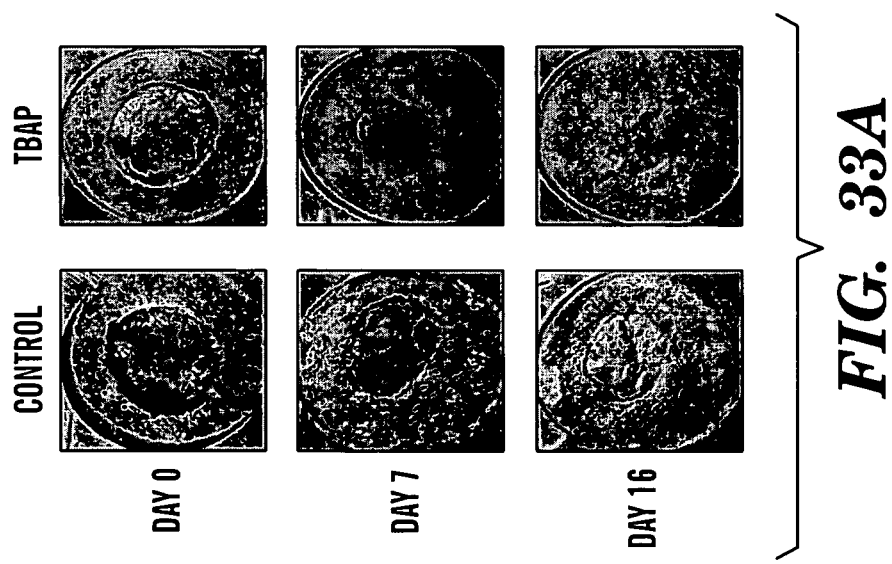
Figure 34:
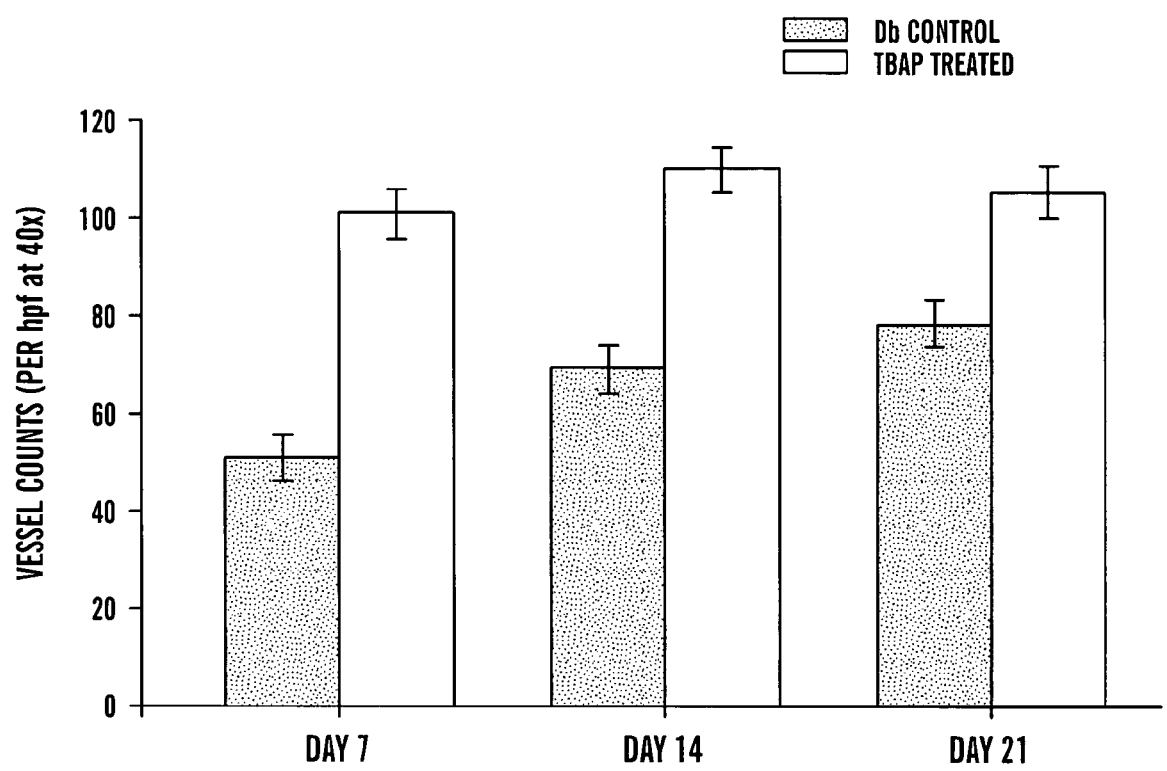
FIG. 34 shows the CD 31 positive blood vessel counts in diabetic mice (Db control) and diabetic mice treated with MnTBAP (TBAP Treated). The y-axis shows the CD 31 positive blood vessel counts per hpf.
Figure 35:
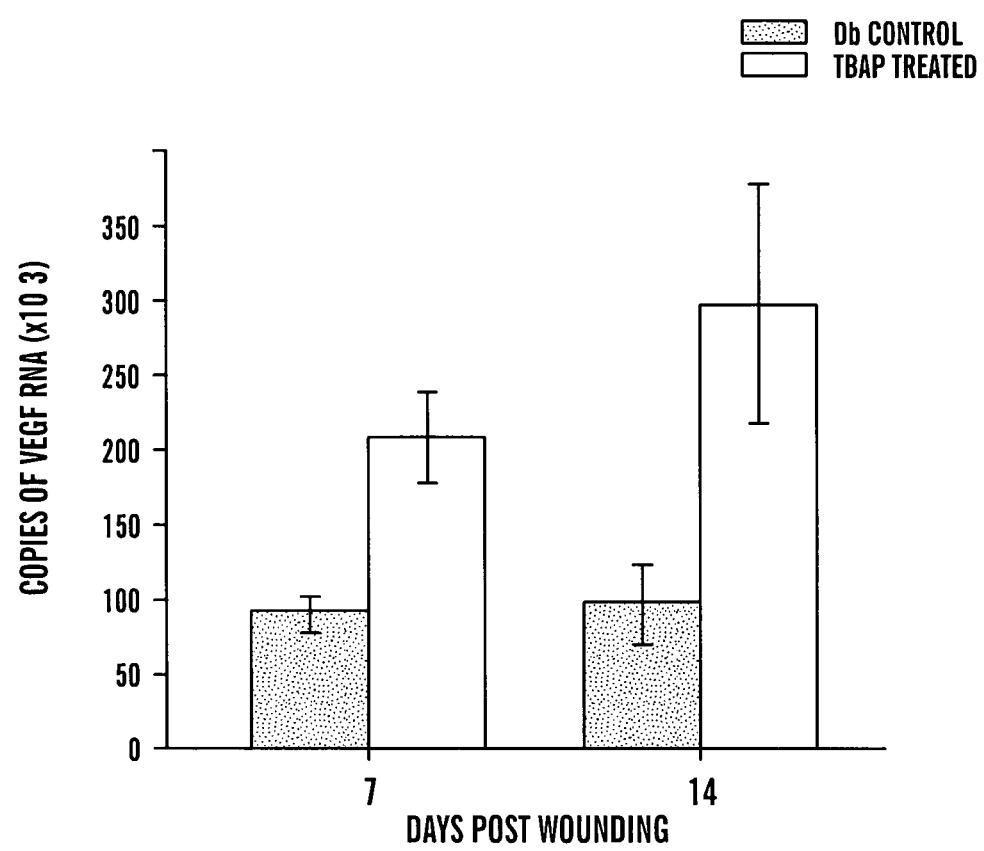
FIG. 35 shows the levels of VEGF RNA after treatment with MnTBAP (TBAP Treated) or no treatment (Db Control). The y-axis shows the number of copies of VEGF RNA in thousands.

The effect of reducing the oxidative stress on wound healing in diabetic mice (db/db) by treating them with MnTBAP, a superoxide mimetic was also studied. The animals were injected with 10 mg/kg intraperitoneally 7 days prior to wounding and throughout the experiment. Treated animals demonstrated complete wound closure at day 16 whereas untreated db mice did not close their wounds until day 26 (FIGS. 33A-B). Neovascularization was also significantly improved with CD31 positive blood vessel counts in the treated groups double those in the control cohort, as shown in FIG. 34. Local angiogenic factors (such as VEGF) were restored to normal levels in the treated animals. Wound VEGF RNA levels were two fold higher in the treated group at day 7 and three fold higher at day 14, as shown in FIG. 35. Diabetic fibroblasts cultured in vitro with MnTBAP demonstrated the ability to upregulate VEGF normally. Thus, the reduction of oxidative stress in diabetic animals normalizes wound healing by restoring local angiogenic factors and vascular growth in the diabetic state.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

What is claimed:

1. A method of treating a foot ulcer in a diabetic subject, said method comprising:
    administering deferoxamine to the diabetic subject having a foot ulcer in an amount and manner effective to heal said foot ulcer.

2. The method according to claim 1, wherein said administering is carried out transdermally.

3. The method according to claim 1, wherein said administering is carried out intravenously.

4. The method according to claim 1, wherein said administering is carried out intraperitoneally.

5. The method according to claim 1, wherein said administering is carried out topically.

6. The method according to claim 1, wherein the deferoxamine is administered with a pharmaceutically acceptable carrier, excipient, and/or stabilizer.

7. The method according to claim 1, wherein the subject is human.

8. A method of treatment, comprising administering a deferoxamine derivative to a diabetic subject having a non-healing foot ulcer in an amount and manner effective to heal said non-healing foot ulcer wherein said deferoxamine is selected from the group consisting of formamide-deferoxamine, acetamide-deferoxamine, propylamide-deferoxamine, butylamide-deferoxamine, benzoylamide-deferoxamine, succinamide-deferoxamine, methylsulfonamide-deferoxamine and hydroxyethyl starch (HES)-deferoxamine.

9. The method of claim 8 wherein the deferoxamine derivative is administered by intravenous injection or transdermal injection.

10. The method of claim 8, wherein the deferoxamine derivative is administered intraperitoneally.

* * * * *